(12) United States Patent
Glimp et al.

(10) Patent No.: US 7,720,692 B2
(45) Date of Patent: May 18, 2010

(54) PROVIDING STANDARDIZED MEDICAL TRIAGE

(75) Inventors: Thomas H. Glimp, Barrington, IL (US); Troyt M. Victorson, Mundelein, IL (US)

(73) Assignee: Medcor, Inc., McHenry, IL (US)

( * ) Notice: Subject to any disclaimer, the term of this patent is extended or adjusted under 35 U.S.C. 154(b) by 537 days.

(21) Appl. No.: 10/985,850

(22) Filed: Nov. 9, 2004

(65) Prior Publication Data
US 2006/0100909 A1    May 11, 2006

(51) Int. Cl.
*G06Q 10/00* (2006.01)
*G06F 19/00* (2006.01)

(52) U.S. Cl. .............................................. 705/2; 705/3
(58) Field of Classification Search ....................... 705/2
See application file for complete search history.

(56) References Cited

U.S. PATENT DOCUMENTS

| | | | |
|---|---|---|---|
| 5,277,188 A | 1/1994 | Selker | |
| 5,471,382 A | 11/1995 | Tallman et al. | |
| 5,764,923 A | 6/1998 | Tallman et al. | |
| 5,964,700 A | 10/1999 | Tallman et al. | |
| 6,014,626 A | 1/2000 | Cohen | |
| 6,047,259 A | 4/2000 | Campbell et al. | |
| 6,049,794 A | 4/2000 | Jacobs et al. | |
| 6,139,494 A | 10/2000 | Cairnes | |
| 6,198,394 B1 * | 3/2001 | Jacobsen et al. | 340/573.1 |
| 6,256,613 B1 | 7/2001 | Falchuk et al. | |
| 6,272,472 B1 | 8/2001 | Danneels et al. | |
| 6,334,192 B1 | 12/2001 | Karpf | |
| 6,353,817 B1 | 3/2002 | Jacobs et al. | |
| 6,383,135 B1 * | 5/2002 | Chikovani et al. | 600/300 |
| 6,687,685 B1 | 2/2004 | Sadeghi et al. | |
| 6,748,353 B1 | 6/2004 | Iliff | |
| 6,757,898 B1 | 6/2004 | Ilsen et al. | |
| 6,767,325 B2 | 7/2004 | Iliff | |
| 6,786,406 B1 * | 9/2004 | Maningas | 235/385 |
| 6,849,045 B2 | 2/2005 | Iliff | |
| 7,011,629 B2 | 3/2006 | Bulat | |
| 7,076,436 B1 | 7/2006 | Ross, Jr. et al. | |
| 7,300,402 B2 | 11/2007 | Iliff | |
| 2002/0029154 A1 | 3/2002 | Majoor | |

(Continued)

FOREIGN PATENT DOCUMENTS

WO    WO 2004/063907 A2    7/2004

OTHER PUBLICATIONS

Sheila Quilter Wheeler with Judith H. Windt; *Telephone Triage: Theory, Practice & Protocol Development*; Delmar Publishers, Inc., Albany, New York; 1993; chapters 1, 4 and 5 (pp. 3-23 and 73-171).

(Continued)

*Primary Examiner*—Robert W Morgan
(74) *Attorney, Agent, or Firm*—Nathan O. Greene; Brinks Hofer Gilson & Lione

(57) ABSTRACT

A triage category for determining a medical triage disposition includes a set of tiered triage questions comprising a plurality of only yes/no questions arranged in a plurality of tiers. The tiers are ranked according to a level of urgency. There is also a plurality of dispositions corresponding to the plurality of tiers. One of the plurality of dispositions is selected when one of the plurality of only yes/no questions is answered "yes."

34 Claims, 23 Drawing Sheets

U.S. PATENT DOCUMENTS

| | | |
|---|---|---|
| 2002/0029157 A1 | 3/2002 | Marchosky |
| 2002/0082144 A1 | 6/2002 | Pfeffer |
| 2002/0138306 A1 | 9/2002 | Sabovich |
| 2003/0036683 A1 | 2/2003 | Kehr et al. |
| 2003/0050539 A1 | 3/2003 | Naghavi et al. |
| 2003/0055679 A1 | 3/2003 | Soll et al. |
| 2003/0092972 A1 | 5/2003 | Mantilla et al. |
| 2003/0097278 A1 | 5/2003 | Mantilla et al. |
| 2003/0158467 A1 | 8/2003 | Liebert |
| 2003/0208377 A1 | 11/2003 | Argenbright et al. |
| 2003/0212575 A1 | 11/2003 | Saalsaa et al. |
| 2004/0073459 A1 | 4/2004 | Barthell |
| 2004/0078223 A1 | 4/2004 | Sacco et al. |
| 2004/0122295 A1 | 6/2004 | Hatlestad et al. |
| 2005/0060186 A1 | 3/2005 | Blowers et al. |
| 2005/0060187 A1 | 3/2005 | Gottesman |
| 2005/0203828 A1 | 9/2005 | Lyakovetsky |

OTHER PUBLICATIONS

Examination Report from corresponding New Zealand Application No. 554827, dated Jan. 29, 2009 (2 pages).

Examiner's Report from corresponding Canadian Application No. 2,586,839, dated May 20, 2009 (5 pages).

Office Action from corresponding U.S. Appl. No. 10/985,724, dated Jul. 8, 2009 (18 pages).

Office Action from corresponding U.S. Appl. No. 10/985,732, dated Jul. 2, 2009 (19 pages).

Unknown author, "Problem Knowledge Couplers: A Problem Oriented Approach to the Computerized Patient Record," PKC Corporation, published 1998, pp. 1-1 to 2-17 (retrieved from www.pkc.com/papers/pomr.pdf) (30 pages).

Examination Report from corresponding New Zealand Application No. 554827, dated Aug. 6, 2008 (2 pages).

\* cited by examiner

| DISPOSITION SET 1 (396) | DISPOSITION SET 2 (397) | DISPOSITION SET 3 (398) | DISPOSITION SET 4 (399) |
|---|---|---|---|
| REFERRAL TO PREFERRED MEDICAL PROVIDER OR OTHER PROVIDER | CALLER IS DIRECTED TO A PREFERRED MEDICAL PROVIDER FOR FURTHER EVALUATION AND/OR CARE. | EMERGENT-911 | EMERGENT-911 |
| | CALLER IS DIRECTED TO AN ALTERNATIVE MEDICAL PROVIDER FOR SPECIAL CARE OR IF PREFERRED MEDICAL PROVIDER IS CLOSED. | EMERGENT | EMERGENT |
| | CALLER IS SENT HOME WITH SELF-CARE INSTRUCTIONS. WILL RETURN TO WORK NEXT SHIFT. | URGENT | URGENT |
| | RETURN TO WORK IN MODIFIED DUTY ARRANGED WITH SUPERVISOR AND SELF-CARE INSTRUCTIONS. | NON-URGENT | NON-URGENT |
| SELF-CARE INSTRUCTIONS | CALLER IS GUIDED IN SIMPLE FIRST AID. RETURN TO WORK WITH SELF-CARE INSTRUCTIONS. | ALTERNATIVE DUTY - RETURN TO WORK | SELF-CARE |
| | CALLER ONLY REQUIRES ASSURANCE AND/OR INFORMATION. RETURN TO WORK. | FIRST AID - RETURN TO WORK | |
| | | INFO ONLY - RETURN TO WORK | |

| CRITICAL CONSIDERATIONS 482 | |
|---|---|
| CLINICAL FRAME 484 | |
| TIERED TRIAGE QUESTIONS 486 | QUESTION RATIONALE 488 |
| SELF-CARE<br><br>overview<br><br>self-care instructions      490<br><br>prevention advice<br><br>follow-up questions | |
| FREQUENTLY ASKED QUESTIONS 492 | |
| GENERAL INFORMATION 494 | |

FIG. 8

UPPER EXTREMITY INJURY  ⟵ 480

482 ⟶

*Critical Considerations*

✧ The upper extremity includes both scapula and clavicle
✧ Fracture, joint dislocation, and nerve or vessel injury are conditions to be considered
✧ A fall from a distance equal to or greater than the person's height is more likely associated with serious injury
✧ Open wounds associated with upper extremity trauma should be evaluated with the open wound algorithm

*Clinical Frame* ⟵ 484

Mechanism of injury?
Location of injury?
Time of injury?
Treatment tried/results?

*Triage Questions* ⟵ 486

Emergent-911 Referral Questions: ⟵ 500

|  | YES | NO |
|---|---|---|
| • Exposed bone? | ☐ | ☐ |
| • Amputation (not a superficial digital avulsion)? | ☐ | ☐ |
| • Significant gross deformity? | ☐ | ☐ |
| • Severe pain? | ☐ | ☐ |

Emergent Referral Questions: ⟵ 508

|  | YES | NO |
|---|---|---|
| • More than minor swelling over a joint(s)? | ☐ | ☐ |
| • Significant loss of joint motion not due to pain? | ☐ | ☐ |
| • Significant functional limitation ("things you can't do") with the extremity? | ☐ | ☐ |
| • Numbness ("loss of feeling") below (distal to) the area directly injured? | ☐ | ☐ |
| • Weakness in the hand or arm not due to pain alone? | ☐ | ☐ |

Urgent Referral Questions: ⟵ 514

|  | YES | NO |
|---|---|---|
| • Moderate pain? | ☐ | ☐ |

Non-Urgent Referral Questions: ⟵ 522

|  | YES | NO |
|---|---|---|
| • Persistent mild pain lasting over 72 hours? (If pain meets these conditions, but the pain has been present for <72 hours, patient will be told in self-care instructions to call back if pain persists ≥ 72 hours) | ☐ | ☐ |

FIG. 10A

Upper Extremity Injury Self-Care Instructions —— 490

These self-care instructions are recommended for you at this time based on the information you provided during your triage call. Please contact us if you have any questions or concerns about your condition or if your symptoms worsen.

Overview:
Most hand, wrist and arm injuries are not serious and respond to simple measures and time. However, broken bones, dislocated joints and injury to nerves or blood vessels are possible. Occasionally small wounds that aren't noticed at first can lead to infection later. Serious symptoms include fever, sweats, chills, severe or worsening pain, significant swelling, numbness, and loss of motion or strength not just due to pain.

Treatment:
1. Acetaminophen (Tylenol), Aspirin or Ibuprofen (Advil, Nuprin, Motrin IB, generic) may be taken as needed for pain.
   WARNING! Aspirin or Ibuprofen should NOT be taken if you have or have ever had gastritis or an ulcer!
   WARNING! Ibuprofen must not be taken by individuals with an aspirin allergy!
   WARNING! Aspirin or Ibuprofen must not be taken by pregnant women!
2. Elevate the affected area as much as possible
3. Apply ice to sore areas for 20-30 minutes every two hours while awake for two days.
4. Heat may help, but do not use for 1-2 days after an injury.
   WARNING! Do not sleep on heating pad - you may burn yourself!
5. Work modifications may be appropriate, such as, restricted lifting and forced grasp, etc.

Call back if:
  · Pain persists over 72 hours

See your medical provider or call back for any of the following symptoms:
  · Fever, sweats or chills
  · Redness in the affected limb
  · Numbness or tingling in the affected limb
  · Increased swelling
  · Loss of motion or weakness in the hand or arm not due to pain alone FAQs: —— 492
  Q: *I heard a "pop" - what does that mean? Did I break a bone?*
  A: A "pop" sound is heard with many injuries. Fortunately, it doesn't always mean that there is a broken bone or torn ligament. There are much better ways to determine if significant damage has been done, including serious pain, swelling or loss of function.
  Q: *I have a "knot" - should I be worried?*
  A: A knot is usually a small blood collection (hematoma) under the skin. This can occur with both serious and minor injuries. Often the knot is associated with blue or purple discoloration, which later changes to green, yellow and brown as the clot is broken down by your body. It may take weeks or even months to completely go away. A hematoma is not the type of blood clot that is serious and can spread to the lungs.

| QUANTIFYING WOUND DEPTH | | |
|---|---|---|
| | Symptoms/Observation | Injury Mechanism |
| *Wound Depth* — Likely to be Deep | • Loss of movement (not from pain alone, for example not able to move a finger after a cut to the hand)<br>• Loss of sensation distal to the wound<br>• Wound edges continually opening, gaping widely or not coming together<br>• Fat, muscle or other tissue visible in the wound<br>• Foreign body that cannot be easily and completely removed<br>• Loss of consciousness (scalp wound)<br>• Shortness of breath (trunk wound) | • Fall onto or against a hard surface<br>• Injury from sharp object<br>• Stabbing-type injury<br>• Penetrating injury<br>• Missile wound, e.g., bullet, nail from nail gun, debris from grinding wheel |
| Less Likely to be Deep | • Local pain but no other symptoms | • Slash, scrape, abrasion, avulsion<br>• Injury from blunt object |

← 598

Copyright (c) 2004 Medcor, Inc.

PROVIDING STANDARDIZED MEDICAL TRIAGE

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

Originally, medical triage was a process deployed during wartime or disasters by which a nurse or other medical professional personally performed an initial assessment of patients to group them into one of three categories: those too ill to benefit from immediate medical care, those well enough to survive without immediate care, and those who could benefit from immediate care. In situations in which immediate medical care was a scarce resource, triage methodology helped ensure that such care would be allocated rationally, for maximum aggregate benefit.

In a broader sense, medical triage is a process for sorting people with medical complaints into groups based on the likelihood of them benefiting from particular levels of medical treatment. For example, most hospital emergency rooms utilize some kind of triage methodology to determine the priority in which patients receive care. The methodology can also include a decision-making strategy for deciding whether a nurse is able to dispense an adequate level of care or a physician is required for a higher level of care. Much of this is done in person, using medical assessments such as blood pressure, pulse, skin color, and general observations of the patient to supplement what the patient describes about his or her condition. The staff then applies hospital triage rules based on that information to determine treatment priority and a level of care, typically aiding those with the most serious conditions first.

Such medical triage systems exist to ensure that an appropriate level of care is dispensed to all individuals, by evaluating the significance of their self-reported or observed symptoms and matching them with a particular level of care. Accurate triaging means that the patient's medical concerns receive a suitable level of medical attention—neither substantially more nor substantially less than what he or she needs.

Triage systems can also ensure that the dispensation of care is more economically efficient. In this age of ballooning medical costs, a medical triage system can mean that whoever ultimately pays for the medical services (e.g., government, companies or individuals) does not pay for an unnecessary level of treatment. For example, if someone with a minor injury is accurately triaged, an appropriate level of care can be determined, while expensive services, such as ambulance transport and emergency department care, can be avoided, if unnecessary.

Some triage systems are focused on controlling and limiting utilization of medical services (i.e., gate keeping). These triage systems are operated by or paid for by insurance companies and/or third party administrators responsible for general health care costs. The system guides callers to medical generalists, rather than to more costly specialists, except when a specialist is necessary. These systems will also direct referrals to in-network (i.e., discounted) medical providers, steering callers away from out-of-network (i.e., non-discounted) providers.

The spread of telecommunications means that some types of medical triage can be employed by persons who are not on-site with the patient. Advances in triage methods have enabled persons without extensive medical training to conduct some types of triage, so long as they are trained in the triage methods. A common form of triage that is conducted telephonically and by non-medical professionals with specialized training is that used by 911 Emergency Medical System (EMS) dispatching services. However, these services generally operate under the assumption that some emergency medical response will be sent to all callers. The dispatcher typically determines the level of response (e.g., whether basic or advanced life support is dispatched, which ambulance or other responder is closest to the caller, and which caller 105 gets priority when there are multiple simultaneous calls). EMS dispatchers also provide pre-arrival instructions, guiding callers in simple life saving techniques to help stabilize patients until emergency personnel arrive.

Medical providers, including clinic and hospital departments, may also utilize a triage service for screening purposes. For example, many expectant mothers and parents call obstetricians' and pediatricians' offices with a variety of medical complaints, concerns and questions. A triage service can play a role in determining which patients need to see a physician and which do not. Many clinics use their own staff for this triage service, but other clinics out-source to call centers. Similarly, many doctors' offices, clinics and hospital departments use call centers to answer their telephones on weekends and after business hours. In addition to handling scheduling and message services, these call centers often use a level of triage to determine which calls warrant paging an on-call doctor.

Most triage calls begin with a nurse recording the medical condition or injury as stated by the caller, along with the caller's demographic information. This is followed by questioning by the nurse and a short health history. The nurse will assess the symptoms, provide information on seeking care and improving symptoms, and refer the caller to a physician, if necessary. Documentation of the call can be the final part of the triage process.

Many of the existing services described above provide a triage service in which nurses apply a variation of the free-form triage, answering callers' medical questions using the nurse's own expertise or general guidelines. While sample protocols, risk factors and other information can be provided, these systems do not establish a broadly applicable and consistent decision-making process. Nurses are left to formulate their own questions and direct their own investigations. Even with general guidelines such a system can be rife with inconsistencies and other limitations. Each nurse can have his or her own particular predilections and can steer the inquiry in a direction not warranted by a fuller understanding of a particular patient's condition or optimal practices obtained by methodical study of prior triage cases. The nurse can miss critical points as a result of sloppiness or lack of knowledge and can, as a result, direct more treatment or less treatment than is appropriate. It can be impossible to ensure consistency and quality control with this kind of system.

SUMMARY

The invention relates to a medical triage system.

A triage category for determining a medical triage disposition includes a set of tiered triage questions comprising a plurality of only yes/no questions arranged in a plurality of tiers. The tiers are ranked according to a level of urgency. There is also a plurality of dispositions corresponding to the plurality of tiers. One of the plurality of dispositions is selected when one of the plurality of only yes/no questions is answered "yes."

Other systems, methods, features and advantages of the invention will be, or will become, apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The invention can be better understood with reference to the following drawings and description, with emphasis placed upon illustrating the principles of the invention.

FIG. 5 shows a chart depicting four exemplary disposition sets.

FIG. 8 is a schematic depiction of a format for a triage category.

FIG. 10A shows an exemplary triage category for upper extremity injuries, including a set of tiered triage questions and corresponding dispositions.

FIG. 10B shows exemplary self-care instructions, follow-up criteria and frequently asked questions associated with the triage category in FIG. 10A.

FIG. 13 shows a sample quantification tool for standardizing and defining triage questions and responses.

DETAILED DESCRIPTION

The Triage Platform

Figure 1:
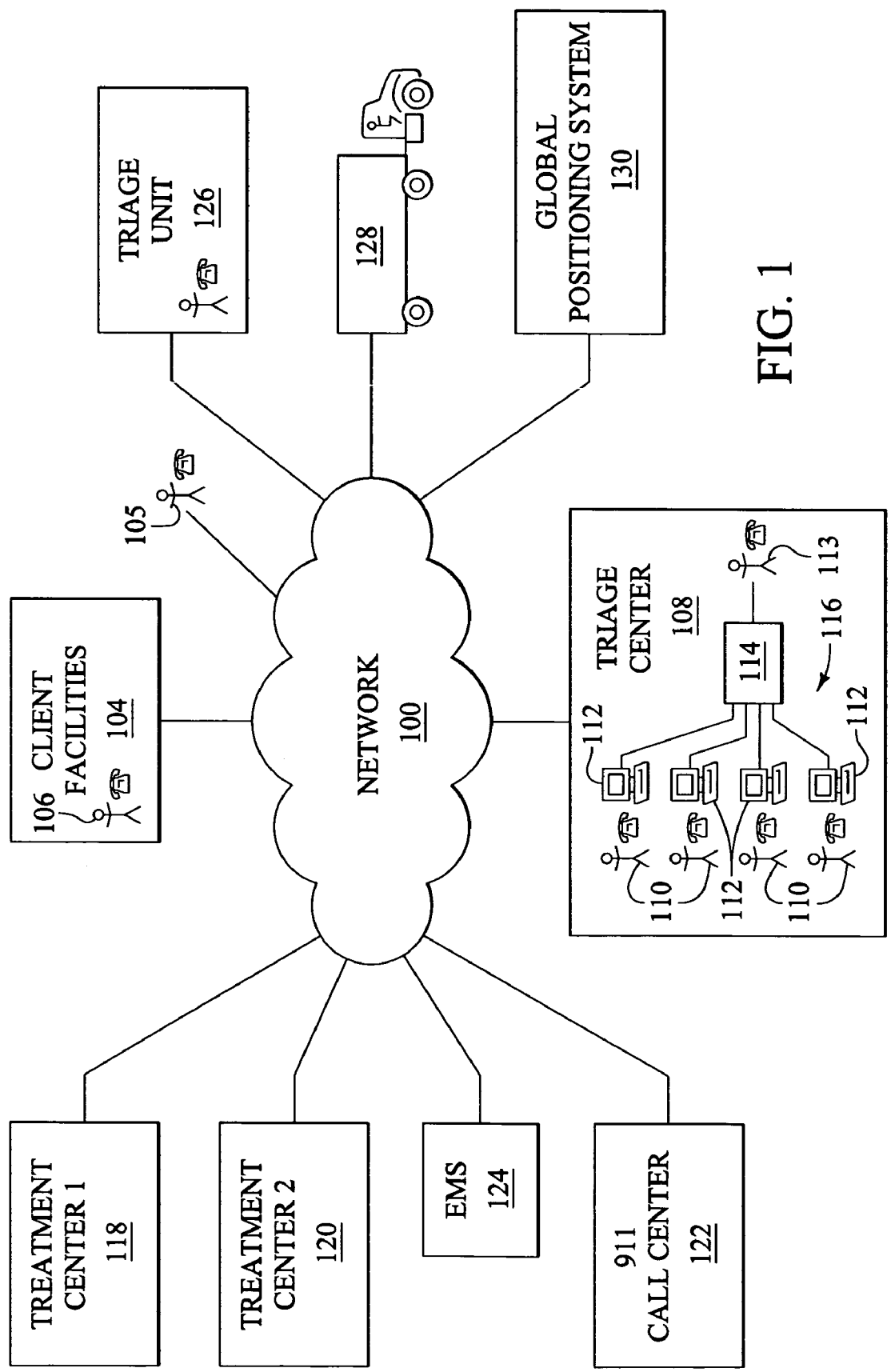
FIG. 1 is a schematic depiction of a platform for implementing triage.

A schematic overview of a platform for implementing a triage system of the invention is shown in FIG. 1. Elements used in supporting and implementing the triage system can be connected through a communications network 100, including, for example, the Internet, an intranet, a local area network and/or a wide area network. Additional elements not shown in FIG. 1 can be included in such a platform. The triage system can also be implemented with fewer elements than shown in FIG. 1.

The triage system can address the medical inquiries of individuals in any context in which injury management and triage is desirable. Application of the triage system can help reduce utilization of expensive, and often unnecessary, appointments with physicians and emergency room visits. By eliminating unnecessary physician appointments and visits to the emergency room, the system can also reduce unnecessary recordable injuries and unnecessary claims for Workers' Compensation. The triage system can also help ensure prompt, appropriate care, thereby mitigating additional injury, reducing an individual's time away from work and preventing permanent disabilities. There can be direct cost savings by directing an individual to a preferred treatment center (where permitted by law) in which care is more appropriate or better tailored to the individual's condition, and, in some cases, less expensive. The system can also encourage those who are ordinarily reluctant to seek medical care to seek such care when they might benefit from it.

The triage system can include one or more triage centers 108 in which one or more triage operators 110 communicate with individuals (e.g., a caller 105) who have contacted the triage center 108 with medical concerns or questions. The triage operator 110 can be in contact with the caller 105 through the communications network 100 (e.g., using telephones) to allow for a remote triage investigation. The triage operator 110 can work from anywhere he can connect to the communications network 100, including from a triage unit 126, which can be connected through the communications network 100 to the triage center 108. The triage operator 110 can also operate independently, for example, using a non-networked PC.

In other cases, however, the triage can be implemented in part by a computer system 116, using voice recognition to process the answers offered by the caller 105 and/or using voice generation to present the questions to the caller 105 over the telephone or similar device. A computer system 116 can also present the questions in written form to the caller 105, as in an Internet Web page, for example. The triage process can be implemented automatically using some of the above-mentioned techniques.

The triage operator 110 can be a physician, surgeon, medical resident, physician assistant, nurse practitioner, registered nurse, paramedic, psychiatrist, dentist, pharmacist, other medical professional or other person trained to implement the triage system. In some cases, non-medically trained people can implement the triage system, if they are properly trained to implement the triage system. It can be more efficient to use registered nurses, because they are often trained in general triage practices, can have relevant and useful general medical knowledge and experience to place triage instances into context, and because their services can be less expensive than those of physicians. Someone with credentials less than those of a registered nurse can be utilized as the triage operator 110, although adequate supervision of lesser skilled triage operators 110 may be desirable to ensure that the triage process is accurately implemented. Applicable laws and regulations in certain jurisdictions may require minimum licensure or credentials separate from what the triage system requires in order to provide medical advice or triage service in that jurisdiction.

The caller 105 can be anyone who makes contact with the triage operator 110 or computer system 116 for the purposes of medical triage. The caller 105 can be the injured or ailing person, or anyone with medical questions. The caller 105 can also be someone who is assisting the injured or ailing person, especially in situations where the injured person is not able to call or communicate over the telephone. For example, a supervisor can help an employee place such a call if the employee is partially incapacitated. A supervisor can also place the call on behalf of someone else when company policy so requires. For simplicity, it can be assumed herein that the caller 105 is the person with the medical issue or complaint.

The caller 105 can use a telephone to call the triage center 108 or triage unit 126, such as by using a toll-free (e.g. 1-800) number. The caller 105 can also use a mobile telephone, satellite telephone, walkie-talkie, computer via the Internet or other network, email, BLACKBERRY (Waterloo, Ontario), facsimile machine, two-way pager or any other system for communicating from a remote location to the triage operator 110.

In some situations, the triage system is provided to a client organization to serve its employees, customers, and/or those at its facilities 104. A caller 106 at the organization facilities 104 can be an employee or customer of the client organization, or can have no relation with the client other than being on its property. The client organization can also extend the application of its triage program to callers 105 who are employees, including those off-site and/or not on the job. Additional cost savings can result from improved productivity and morale, as a result of the prompt medical attention available to an employee. Employees can be more satisfied with the level of care and thus more likely to comply with self-care instructions, and can be less likely to initiate litigation against the client organization. Furthermore, by shifting the medical decision-making from the client organization to the triage system provider, the risks inherent in medical decision making are shifted away from the client organization.

A caller 128 who is mobile can contact a triage operator 110 from multiple locations. For example, a long-haul truck driver can have access to the triage system by contacting the triage center 108 or triage unit 126 though the communications network 100 using any of the devices mentioned above. The position of the mobile caller 128 can be determined with a tracking system such as the Global Positioning System (GPS) 130. This can assist in dispatching medical services to the mobile caller 128 and/or directing the mobile caller 128 to a nearby treatment center 118, 120. GPS software employed by the triage operator 110 can help interpret and present GPS-related data for the purpose of locating a mobile caller 128. For example, the position of the mobile caller 128 could be displayed on a display device 160 so that the triage operator 110 or computer system 116 could help identify routes to a treatment center 118, such as the nearest treatment center, or direct an appropriate medical provider to the mobile caller 128.

A caller 105 may require emergency assistance, such as assistance provided by an Emergency Medical Service ("EMS") 124. A call to the 911 call center 122 can be made by the caller 105 at the instruction of the triage operator 110 if the triage disposition so warrants. The 911 call center 122 can in turn dispatch an ambulance by contacting the EMS 124, which will transport the caller 105 to a treatment center 118, 120.

Alternatively, the situation may not require emergency attention. In that case, the triage operator 110 or caller 105 can make an appointment for the caller 105 to see a medical provider (such as a physician, physician's assistant, nurse practitioner, dentist, nurse practitioner, nurse or other medical professional) at one of the treatment centers 118, 120. Treatment centers 118, 120 include hospitals, clinics or other locations where medical care can be dispensed. One or more treatment centers 118 can be identified as a preferred treatment center, based on the client specifications, the proximity of the treatment center 118 to the caller 105 or client facility 104, the known capabilities of the treatment center 118, etc. However, the system can comport with any applicable laws and regulations that govern (or prohibit) the restriction to, or selection of, preferred treatment centers. The triage operator 110 or caller 105 can first attempt to use or contact a preferred treatment center 118; if that fails, he can then attempt to use or contact another treatment center 120.

Computer System

As shown in FIG. 1, the triage operator 110 can use a computer system 116 to help implement the triage system. Alternatively, the triage system can be implemented without computers, such as with books. The computer system 116 can be a client-server system, in which one or more computer clients 112 send requests to a server 114 and a server 114 responds to requests from one or more computer clients 112. A "computer client" can be broadly construed to mean computer hardware that requests or receives the file, and "server" can be broadly construed to be the computer hardware that provides or downloads the file. The computer system 116 can include a personal computer (PC), laptop computer, server, workstation, and the like, running any one of a variety of operating systems.

The computer client 112 can be any computer hardware, such as a PC, workstation, hand-held device, electronic book, personal digital assistant, peripheral, etc. The computer client 112 can also be a software program running on a computer directly or indirectly connected or connectable in any known or later-developed manner to any type of computer network, such as the Internet. For example, a representative computer client 112 is a personal computer that is PENTIUM-based (Intel, Santa Clara, Calif.) and includes an operating system such as MICROSOFT WINDOWS (Microsoft Corp., Redmond, Wash.). The computer client 112 can also include a Web browser, such as INTERNET EXPLORER (Microsoft Corp., Redmond, Wash.). A computer client 112 can also be a notebook computer, a handheld computing device (e.g., a PDA), an Internet appliance, a telephone, or any other such device connectable to the computer network or other communications network.

The server 114 can be any computer hardware, such as a computer platform, an adjunct to a computer or platform, or any component thereof, such as a program that can respond to requests from a computer client 112. For example, the server can be a PENTIUM-based computer (Intel, Santa Clara, Calif.) running WINDOWS 2000 SERVER and executing MS SQL (Microsoft Corp., Redmond, Wash.) or ORACLE (Oracle Corp., Redwood Shores, Calif.). The server 114 can also include a display supporting a graphical user interface (GUI) for management and administration, and an Application Programming Interface (API) that provides extensions to enable application developers to extend and/or customize the core functionality thereof through additional software programs.

The triage system can be implemented using software running on the computer system 116. In addition, the triage system can be implemented using a transmission medium, such as one or more carrier wave signals transmitted between the computer system 116 and another entity, such as another computer system, a server, a wireless network, etc. The triage system can also be implemented using an API or a user interface.

Computer Hardware Components

Figure 2:
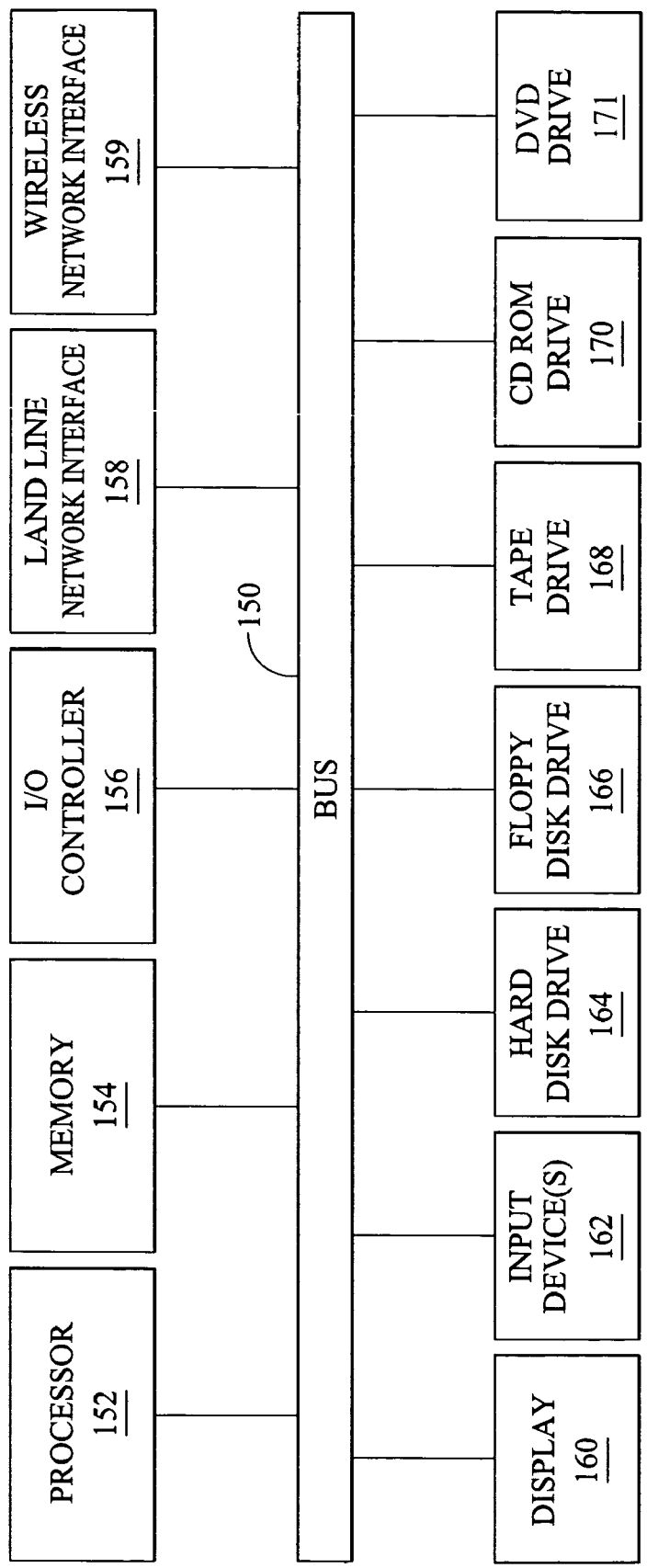
FIG. 2 is a block diagram showing the possible hardware components of a computer system for implementing triage.

A block diagram of the computer system 116 is shown in FIG. 2, showing a number of different hardware components coupled by a data bus 150 to allow communication therebetween. The components can communicate via hardwire or wireless connections. The computer systems embodying the triage system need not include every element shown in FIG. 2, and equivalents to each of the elements are intended to be included within the spirit and scope of the triage system.

The central processor 152 shown in FIG. 2 can run software that assists in triaging the caller 105. The central processor 152 can, for example, be used to process information entered by a triage operator 110 into the computer system 116. The central processor 152 can be any type of microprocessor, such as a PENTIUM processor (Intel, Santa Clara, Calif.).

A main memory unit 154 can also be a part of the computer system 116. Additional storage devices, such as a fixed or hard disk drive unit 164, a floppy disk drive unit 166, a tape drive unit 168 and/or optical storage devices such as a CD Rom drive 170 or a DVD drive 171 can act as adjuncts and/or alternatives to the main memory unit 154. The storage devices, such as the DVD drive 171, in addition to the main memory unit 154, can be used for storing and access to recordings of the conversations between the caller 105 and the triage operator 110, medical and other data related to the caller 105, triage-related software and data used to execute the triage-related software.

The network interface 158, 159 can be any type of a device, card, adapter, or connector that provides the computer system 116 with network access to a computer or other device, such as a printer. In the triage system, the network interface 158, 159 can enable the computer system 116 to connect to a computer network such as the Internet or Ethernet. Software and data can also be loaded into the computer system via the network interface 158, 159.

A display device 160 can be used to display, to the triage operator 110 or others, any information related to the triage system, such as triage questions to ask of the caller 105. The display device 160 can be any type of display, such as a liquid crystal display (LCD) and the like, capable of displaying, in whole or in part, the triage categories or other outputs generated by the computer system 116.

One or more input devices 162 allow the triage operator 110 to enter information into the computer system 116, such as answers to triage questions. The input device 162 can be any type of device capable of providing the inputs described herein, such as keyboards, numeric keypads, touch screens, pointing devices, switches, styluses, scanners and light pens. An input/output controller 156 can support the input and output devices.

Database and Software Components

Figure 3:
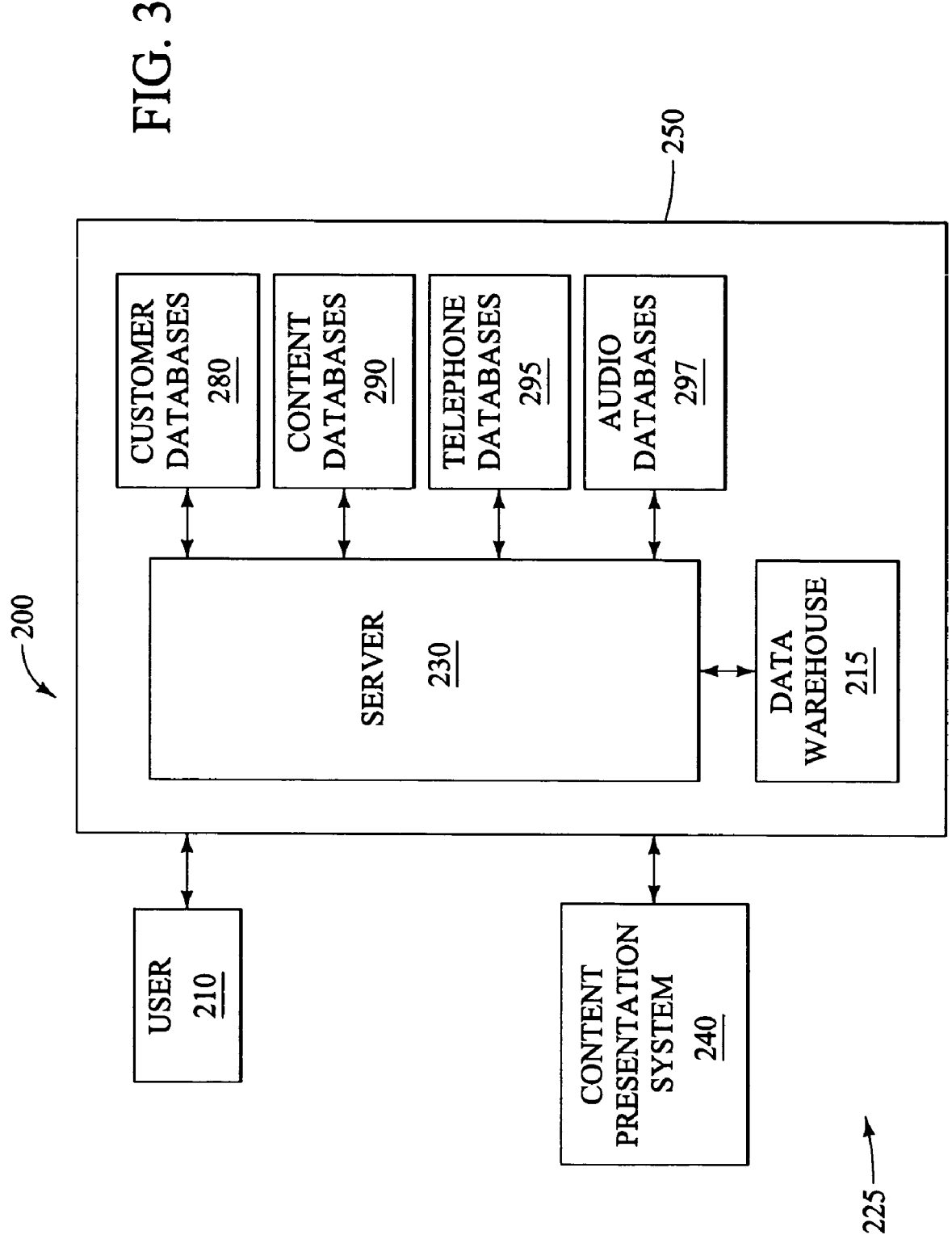
FIG. 3 is a block diagram showing possible database components in a computer system for implementing triage.

FIG. 3 is a block diagram showing possible database components and supporting architecture in a computer system 200 for implementing the triage system. In the system of FIG. 3, a user 210 can interact with a back end 250 of the computer system 200 via a server 230 and a content presentation system 240. The computer system 200 can include one or more customer databases 280, one or more content databases 290, one or more telephone databases 295 and one or more audio recordings databases 297 and a data warehouse 215. The back end 250 can be located in a triage center 108 or off-site.

The user 210 can be a triage operator 110 capable of interacting with the computer system 200. The user 210 can also be someone who inputs or accesses data or triage-related information, updates the software in the computer system 200, or otherwise alters the computer system 200. The user 210 can also be someone who mines the data in the computer system 200 to generate reports, such as call statistics, injury reports and other reports. The user 210 can include a client or representative thereof, who can generate and/or have instant and secure access to statistical reports on employee call characteristics, incident rates and other parameters via the communications network 100.

The user 210 can access the computer system 200 through the Internet, a remote server, or a networked device through, for example, a server 230. Users 210 may also access the computer system 200 users using a wide area protocol (WAP), digitized voice signals, interactive television signals, electronic mail systems, voice mail, direct mail, and various messaging systems, including short message service (SMS) systems. The user 210 may also interact directly with the back end 250. Access to the back end 250 can also be provided via one or more carrier wave signals that are accessible to the user 210 without requiring a server 230.

The back end 250 can consist of various elements connected by a LAN. The elements of the back end 250 can include a file server running WINDOWS 2000 SERVER; a database server running MS SQL (Microsoft Corp., Redmond, Wash.) or ORACLE (Oracle Corp., Redwood Shores, Calif.); phone servers running a WINDOWS 2000 platform; fax servers running a WINDOWS 2000 platform (Microsoft Corp., Redmond, Wash.); an e-mail server running MICROSOFT EXCHANGE; and UNIX-based e-mail server running SENDMAIL (Sendmail, Inc., Emeryville, Calif.) for back-up; a web server running IIS (Microsoft Corp., Redmond, Wash.); a reporting engine running CRYSTAL ENTERPRISE (BusinessObjects, San Jose, Calif.); and a NETSCREEN fire wall device (Juniper Networks, Sunnyvale, Calif.). The system can run 128-bit encryption such as VERISIGN (Verisign, Inc., Mountain View, Calif.) to ensure system security. Other elements and software can be added to this back end 250. The back end 250 can also be implemented with ACCESS (Microsoft Corp., Redmond, Wash.), DEVELOPER 2000 (Oracle Corp., Redwood Shores, Calif.), or other reporting tools, including the replacements or successors to these applications.

The architecture of the back end 250 can be a flexible design that includes real-time, database-resident support, permitting reporting capabilities that can take advantage of E-mail/WAP/Voice-based communication. As content is added to the back end 250 (e.g., in content databases 290), the attributes of the content can be delivered to the user 210 in near real time, using, for example a report generated in the data warehouse 215 and presented to the user 210 via the content presentation system 240. The back end 250 can create queries to be provided to a user 210 and can receive responses to the queries. The back end 250 can also perform processing based at least in part on the queries and the responses, along with information stored in its databases and lookup tables, and helps determine the triage disposition.

The computer system 200 can also include a business logic processing system (not shown) connected to the server, to form a three-tier computer system. The business logic processing system can receive queries or responses from the user 210. That information can be used to update the customer databases 280, as well as retrieve data and information from both the customer databases 280 and content databases 290. The business logic processing system can also provide inputs to and receive outputs from the data warehouse 215 and communicate with any rules systems to apply one or more predetermined rules to the user queries. These functions can be accomplished in the absence of a discreet business logic processing system.

The data warehouse 215 communicates with the customer databases 280 and the content databases 290 and other databases during the preparation of reports or triage-related queries which can be provided to the user 210, such as with an on-screen display. The data warehouse 215 can also organize and store data generated using the server 230 and/or a rules system. The databases 280, 290 can be, for example, SQL relational databases and/or relational online analytical processing databases (ROLAP).

The customer databases 280 can include one or more databases for storing data provided by users 210 and/or derived from inputs by users 210, including demographic information, answers to triage-related questions, dispositions, follow-up data, plans, or other inputs from the users 210. The customer databases 280 can have real-time capabilities for support of the data warehouse 215. The MedfilesMOL™ database and the telephone system database described below can be components of the customer database 280.

The content databases 290 can include one or more databases storing content that can be provided to a user 210 during operation of the system. The content databases 290 can include all of the information of the triage categories, including the tiered triage questions and related information, discussed below. The triage database described below may be a part of the content databases 290.

The content databases 290 can include the tiered questions, in addition to data that is "scored" in advance for one or more predetermined characteristics. This is also referred to as "derived" data. The scored data can, for example, be maintained as a set of one or more tables of scores. Certain quantitative or qualitative details about a medical condition can be assigned one or more scores based on severity. Derived data can be used in conjunction with look-up tables to accept queries from the server 230 and provide appropriate responses. For example, a given amount of pain, shortness of breath or extent of burns can be matched with a disposition through the lookup tables. Information in lookup tables can be more quickly and conveniently accessed in certain circumstances.

The telephone databases 295 store and provide access to telephone numbers, associated names and other telephone-related data. The audio databases 297 store digitized recordings of the calls.

The computer system 116 can execute dynamic updates to the screen controls to change one or more properties, without having to make coding changes and/or redeploy the triage-related software. Those properties can include position, size, backcolor, forecolor, border style, field input length and tool tip text. The computer system can also execute dynamic updates regarding whether a field receives focus when a Tab key is pressed and/or the order in which fields receive focus when the Tab key is pressed. These changes can be useful for refining the software to improve work flow and ease of use without having to reprogram the computer system 116.

In the above description of FIG. 3, it should be understood that any portion of the functionality provided by the computer system 200 could be provided by independent systems and/or different groupings of systems than illustrated in FIG. 3.

Triage Process

Figure 4A:
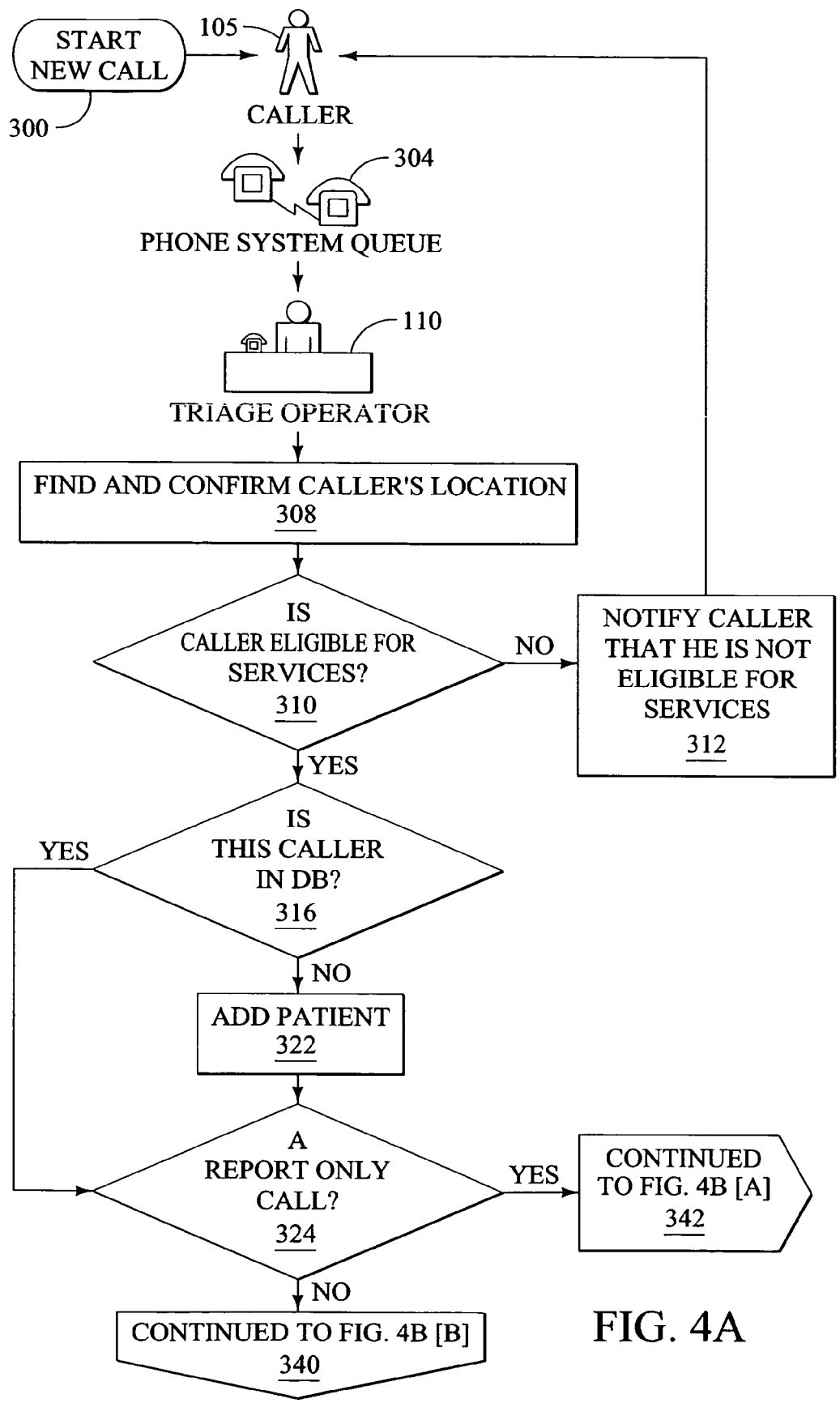
FIG. 4 is a schematic depiction of a call process for the triage system.
Figure 4B:
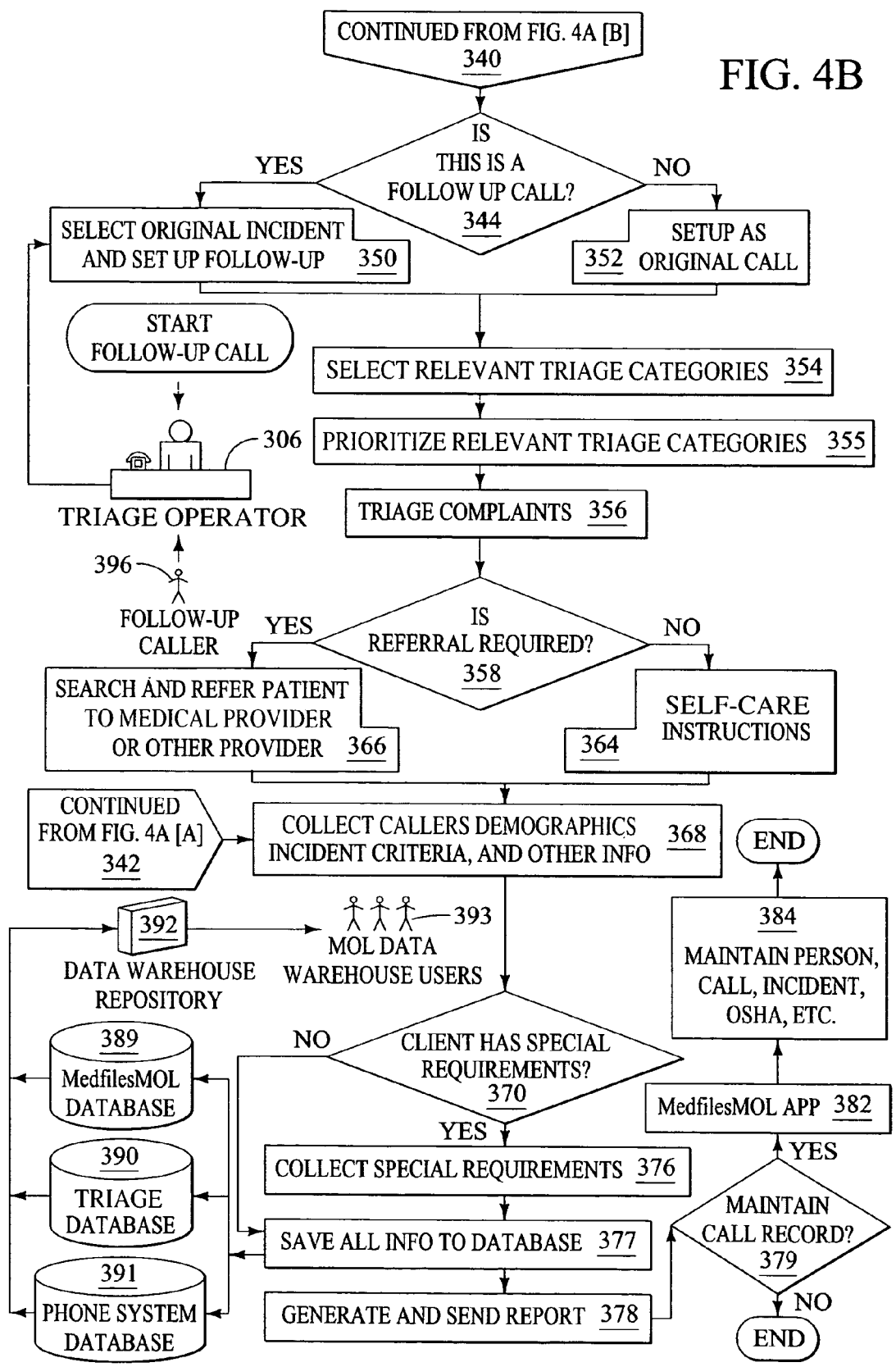

As shown schematically in FIGS. 4A-B, users of the triage system (e.g., callers 105) can contact a triage operator 110 from a remote location. The caller 105 can, depending on the traffic to the triage center 108, be placed in a telephone system queue (step 304) until a triage operator 110 is available. The phone system can require the caller 105 to indicate whether the call is for a new injury; those calls are moved ahead of others in the queue who indicate that they are reporting old injuries. The triage center 108 can be located anywhere a triage operator 110 or computer 116 employs the triage system.

The computer system 116 and software can work together to present the triage operator 110 with information relevant to a caller's medical complaints, prompt for specific questions related to the caller's symptoms, and record the corresponding answers. The triage operator 110 can employ the information and questions within those categories to determine which disposition (i.e., timing and level of medical care) best suits the caller 105, as described in further detail below. The triage system does not necessarily diagnose the caller's medical condition, although the triage system can be used in conjunction with a diagnosis system.

When the caller's turn has arrived, a triage operator 110 can answer the telephone and implement the triage system. All telephone conversations can be digitized and stored digitally on a hard drive and then transferred to DVD; a call can also be stored on analog tape. The call recording and the triage operator's computer inputs can both have a running time-stamp so that they can be linked and/or synchronized to better enable one to understand the basis for the triage operator's decisions or the effectiveness of the triage questions, when analyzed at a later date.

Upon receiving a call, the triage operator 110 can begin by finding and confirming the caller's location (step 308), so that the triage operator 110 can dispatch medical services to the caller's location if necessary. The triage operator 110 can also use the location information to determine if the caller 105 is eligible for services (step 310), e.g. a pre-existing client, employed by a pre-existing client, a customer of a pre-existing client, or otherwise entitled to services. An exemplary computer screen layout shown in FIG. 14A can be suitable for recording such information.

Services can be denied to a caller 105 who is not eligible. If the caller 105 is not eligible for services, he will be notified (step 312). However, if it is apparent that the caller 105 is in need of emergency medical attention, the triage operator 110 can instruct the caller 105 to contact the EMS and provide interim self-care instructions. If the triage operator 110 wishes to contact the EMS on the caller's behalf, it can be important to get an accurate description of the exact location of the caller 105 and information on the appropriate EMS, which the triage operator 110 may not have in the database. Other demographic information such as the caller's social security number or name can be used to determine if the caller 105 is eligible for triage services or has called before, so that his medical records can be accessed, if they exist.

The triage operator 110 can establish whether or not the caller 105 already exists in the triage system database (step 316) using personal data. If the caller 105 does not exist in the database, basic caller data are solicited by the triage operator 110 and entered (step 322) via any appropriate devices, such as a keypad, mouse, light pen, touch screen, scanner, etc. The information can enable the system to follow-up with the caller 105 or allow triage reports to be generated, as described below.

The caller 105 may already be listed in the database. If so, the caller's information is accessed. The exemplary computer screen layout shown in FIG. 14A can be suitable for accessing such information. Once the caller data are entered (step 322) or accessed, the triage operator 110 determines if the call is a report call only (step 324). A report call is a call in which no medical treatment is desired by the caller 105, but merely establishes the caller's data for future contact and for more complete data records of injuries and reporting statistics for triage client organizations. For a report call, intervening triage-related steps are skipped (step 342) and the data collection process is initiated, as described below. The call type can be selected using radio buttons, as described in reference to FIG. 14C, below.

If the call is not a report only call, then the process is continued (step 340), as shown in FIG. 4B, by determining if the call is a follow-up call (step 344). A follow-up call is a call based on a medical condition that was previously addressed by the triage system. If it is a follow-up call, the system is set up as a follow-up call (step 350) by accessing the data related to the original incident, which can be associated with the caller's personal data. This can enable the follow-up call data and the original incident data to be linked within the database, and can help the triage operator 110 understand the earlier incident or condition. A follow-up caller 396 can also contact the triage operator 110 and directly commence follow-up (step 350).

If it is not a follow-up call, the call is set up as an original call (step 352), enabling an initial inquiry into the caller's condition and personal data. The caller's age can be collected in order to determine a suitable level of care for the caller 105. For example, chest pains in a 65-year-old can suggest a heart attack, while they might not for an 18-year-old. If a caller 105 is identified as a minor, a "Pre-Triage for Minors" frame can become enabled, as further described in reference to FIG. 14C, which can give the option of selecting a type of legal consent. Legal consent criteria can be required before the call can progress, in order to prevent the unauthorized triage of minors. A parental consent form on file with the triage center, over-the-phone consent from a parent, or an agreement on file with the client organization can generally allow minors to make full use of the triage system. The triage system can, however, allow for Emergent-911 and Emergent triage of minors under the legal principle of implied consent. Triaging can be discontinued following the Emergent-911 or Emergent questions for minors, as it can become harder to claim that implied consent applies to a less urgent situation. For particular clients, the "Pre-Triage for Minors" frame can be disabled.

Next, the triage operator 110 can select the relevant triage categories (step 354). The categories can correspond to body parts and/or injury types that can be the focus of the triage inquiry. The categories can be generally symptom-based. Each category contains both tiered triage questions and related information. The tiered triage questions, described below, are related questions that can lead to one of a set of possible dispositions, depending on the answers provided. An exemplary computer screen layout that allows selection of relevant categories is shown in FIG. 14C.

The categories that relate to particular body parts can include "abdominal injury," "abdominal pain without injury," "chest pain without injury," "chest injury," "dental injury," "upper extremity pain without injury," "upper extremity injury," "lower extremity pain without injury," "lower extremity injury," "eye injury," "eye chemical exposure," "red eye," "groin strain," "headache, typical," "headache, new onset/atypical," "head injury," "low back injury with direct trauma," "low back injury without direct trauma," "low back pain without injury," "neck injury," "pregnancy," "shortness of breath," etc.

The triage categories that are not necessarily related to a particular body part can include "bites," "blood-borne pathogen exposure," "burns," "electric shock," "frostbite," "general complaint," "heat illness," "insect bite or sting," "insecticide exposure," "open wounds/laceration," "psychiatric conditions/stress," "rash," etc.

As shown in FIG. 4B, the triage operator 110 can ask the caller 105 one or more questions about his complaints to ascertain the origin or cause of the caller's inquiry and allow the triage operator 110 to select the relevant categories (step 354). For example, if the caller 105 states that he fell off a ladder, thereby bumping his head and cutting his arm, the triage operator 110 can select the "head injury" and "laceration" categories. Both the supporting information and tiered triage questions in those two categories—laceration and head injury—can be applied by the triage operator 110 as further described below. If more than one relevant triage category is selected, the categories can be prioritized (step 355). They can be prioritized based on the description the caller 105 provides or rules implemented by the triage operator 110. Such a rule can provide, for example, that the "chest pain" category always has a higher priority than the "groin strain" category.

Both the category selection and the body part selection can be accomplished in the exemplary screen layout displayed in FIG. 14C, where the body part (e.g., foot, neck, hand, torso), body part location 1 and 2 (e.g., left/right/lateral/dorsal) are selected using combo-box fields 672-676, and the category 678 is selected from a list. When the "Add" button 680 is selected, the combination of category and body part are recorded and displayed in a window 682. The same category can be applied multiple times to different areas of the body by selecting the same category a second time while selecting different body parts. For example, the laceration category can be applied to both the hand and the elbow, as primary and secondary body parts. Likewise, different categories can be applied to the same body part, if, for example, there is both a burn and an open wound at the same place. When all or some of the categories and body parts are selected, the triage operator 110 can use the arrow buttons 684 to prioritize the selections, as shown in FIG. 14C.

As shown in FIG. 4B, the information and questions within each of the relevant triage categories are applied to triage the caller's complaints (step 356), i.e., to determine a suitable triage disposition for the caller 105. The possible gradations of disposition can correspond to urgency, as described below, especially with respect to FIG. 5. FIG. 4B shows that the triage operator 110 determines either that a referral is required (step 358) as a result of the triage process (step 356) or not. Thus, there are two basic dispositions shown in FIG. 4B—"requiring a referral" and "not requiring a referral."

If the triage inquiry results in a referral, the triage operator 110 can search for and refer the caller 105 to a preferred medical provider (step 366), including any preferred treatment centers. If there is no preferred medical provider designated by the client, or if the preferred medical provider cannot adequately address the caller's medical condition, the caller 105 can be referred to any other suitable medical provider. Alternatively, the caller 10s can be presented with a list of treatment centers to choose from for referral, or can be allowed to select his own referral clinic, depending on the client policy and applicable laws and regulations. If the triage process does not result in a referral, self-care instructions (step 364) can be given to the caller. An exemplary screen format for displaying triage questions and enabling access to supporting information, including self-care instructions, is shown in FIGS. 14D-E.

If the caller's condition allows, the triage operator 110 can collect more information (step 368) about the caller 105, beyond that requested at the beginning of the call. This information can include demographic data, incident criteria, and other information. An exemplary computer screen format for entering this information is shown in FIG. 14J.

The triage operator 110 can also inquire into other data that is of special interest to the client organization, i.e. the special client requirements (step 370). For example, the client can require that every caller 105 with a back injury be asked if he or she was wearing a company-supplied back-belt at the time of injury. Other clients can require that every caller 105 with a laceration be asked whether he or she was wearing safety gloves. An exemplary computer screen format for entering this information is shown in FIGS. 14M-N.

If there are no such client requirements, or once special client requirements are collected (step 376), the data acquired during the triage process can be saved to a database (step 377). The data can include the identification of the caller 105 and triage operator 110, cause of injury, symptoms, answers to questions, triage disposition, instructions given by the triage operator 110 and the results from caller 105 follow-up, in addition to other information discussed elsewhere.

The databases for saving the post-triage data and the other acquired data include the MedfilesMOL™ database 389, the triage database 390 and the telephone system database 391. The triage database 390 is used for storage and organization of the information obtained during a triage call, and is implemented using an application interface which allows real-time updating and modification of the database. The MedfilesMOL™ database 389 is implemented using a post-call processing software interface that allows the development and editing of the triage software, as well as the investigation of particular call histories. The data in the three databases can be saved for long-term storage in the data warehouse repository 392 (i.e., a data warehouse). Data warehouse users 393 can access the data to prepare reports, study aggregate caller data and study the long-term efficacy of the triage system or elements thereof. The databases 389, 390, 391 and the warehouse 392 can have security features to prevent the unauthorized access to the confidential medical records or proprietary client information contained therein.

Once all of the selected information is saved to one or more of the databases (step 377), a report is generated and sent (step 378) to predetermined recipients. The recipients can include particular contact persons at the client or others, as detailed below.

The system can present an opportunity to maintain the call record (step 379). The client can have instructions not to save such information; if so, the call can be terminated at this point, because the call can be considered complete. If there are instructions to maintain the call record, then the records are saved (step 384) using the MedfilesMOL™ application 382. The MedfilesMOL™ application 382 can be used to maintain demographic information, details about the call and any incident, or other information.

Application of the triage system can result in the selection of a particular disposition from a set of dispositions. A disposition is, generally, the action or actions to be taken by the triage operator 110 or caller 105 to resolve the caller's condition. A particular disposition within a disposition set can be identified by generalized indicia such as numbers or letters to express the selected level of care. For example, a "#1" disposition can indicate the most urgent level of care, indicating to the triage operator 110 that whatever actions are associated with the "#1" level (e.g., calling 911) should be executed. In the same disposition set, a "#5" disposition can indicate the least urgent level of care, indicating to the triage operator 110 that self-care instructions, for example, should be communicated to the caller 105. When general indicia are employed, the specific set of instructions associated with each of the indicia can be modified. Dispositions can also be expressed as the disposition instructions themselves (e.g., "call 911," "see doctor within 24 hours," etc). FIG. 5 shows that the triage system can use a number of triage exemplary disposition sets 396, 397, 398, 399, with varying stratification and level of specificity. These disposition sets 398 can account for differing levels of urgency, from someone who needs immediate medical attention to someone who can treat himself.

Figure 6:
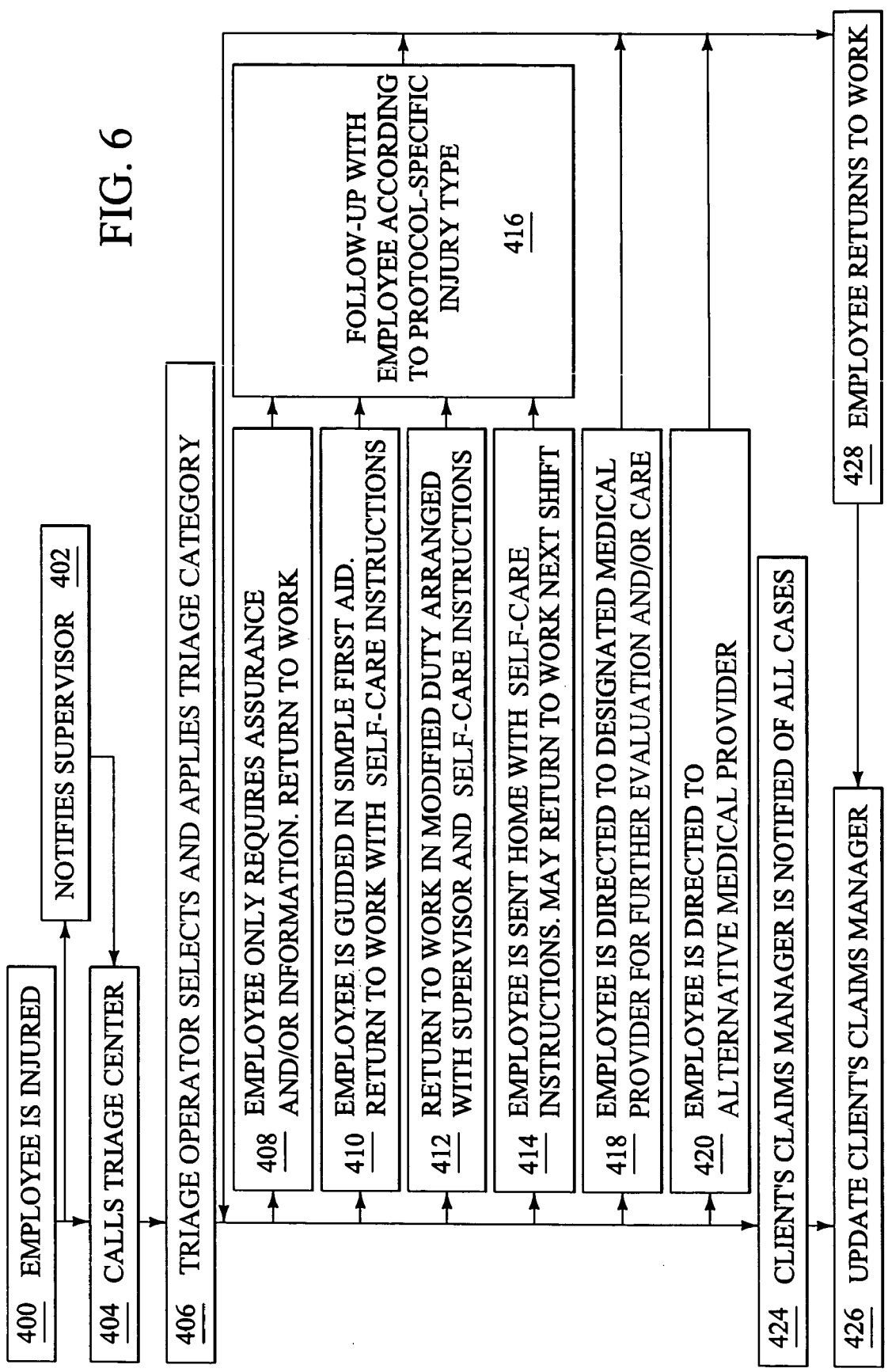
FIG. 6 is another schematic depiction of a call process for the triage system.

FIG. 6 is a schematic depiction of the triage system, and offers a more detailed description of the dispositions that can be assigned to a caller 105 based on the answers given to the triage questions. As shown in FIG. 6, an injured employee (step 400) is directed to notify the supervisor (step 402) so they can call the triage center together (step 404); this step reflects a common corporate policy requiring supervisor involvement following an injury. Otherwise, the employee (step 400) can call the triage center directly (step 404). Once the triage center is contacted, a triage operator 110 can begin to inquire into the details of the injury. This allows the triage operator 110 to select and apply the triage categories (step 406) to assign a disposition.

FIG. 6 shows six possible dispositions, but more or fewer could be used. The first four dispositions (steps 408, 410, 412, 414) are variations on self-care; self-care instructions can be given over the telephone or sent by e-mail or faxed to the caller 105 and his supervisor. For example, one possible disposition is that the employee would require assurance that his condition is not serious and/or information, but would return to work (step 408), after which the triage operator 110 would follow up (step 416) using the particular follow-up information associated with the relevant categories of the previous call. Alternatively, the employee is sent home with self-care instructions and can return to work for the next shift (step 414). If a follow-up is indicated, the system can schedule the follow-up automatically and the caller 105 can be informed to expect a follow-up at a certain date and time. The triage system can be integrated with the calendar function MICROSOFT OUTLOOK (Microsoft Corp., Redmond, Wash.) to automatically schedule and/or document follow-up calls.

If the medical condition of the caller 105 is sufficiently serious, one of the more urgent dispositions (steps 418, 420) is assigned. The caller 105 can be directed to a designated medical facility for further evaluation and/or care (step 418). Also, a caller 105 can be directed to an alternative medical provider if that designated or preferred medical provider is unavailable or cannot effectively address the caller's condition (step 420). The client can specify reasons for which a medical provider is preferred and conditions suitable for overriding that preference, consistent with applicable rules and regulations. For the six dispositions detailed in FIG. 6, the client's claim manager can be contacted about the inquiry (step 424) and updated (step 426), as needed. The software can generate reports that are suited to updating the claim manager and others. The employee will ideally return to work (step 428).

Figure 7:
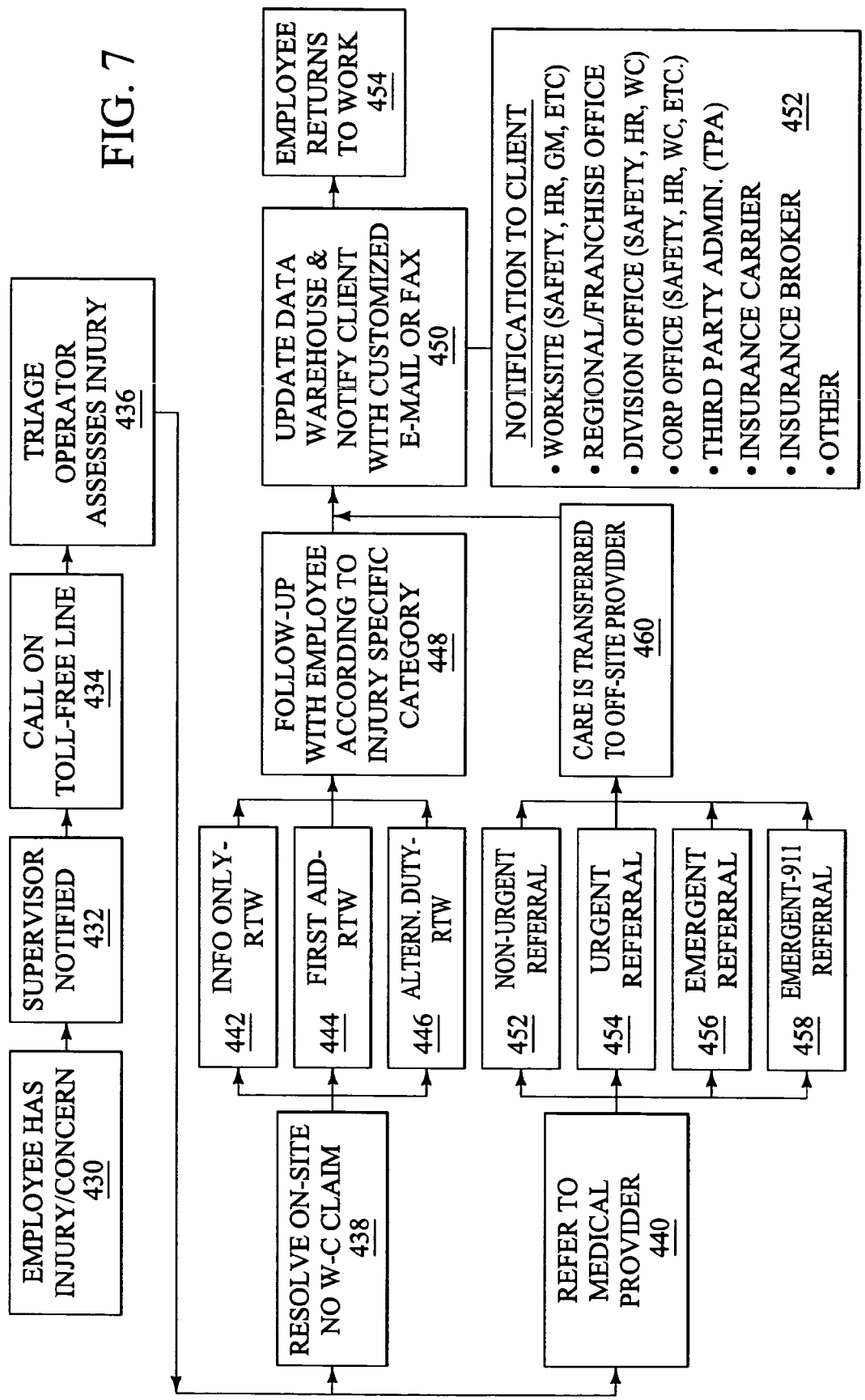
FIG. 7 is a schematic depiction of a call process for the triage system that includes detailed notification procedures.

FIG. 7 shows another schematic depiction of the triage system. The triage process can be initiated with a telephone call to the triage center when an employee has an injury or medical concern (step 430). In this scheme, the supervisor can be notified (step 432) before a toll-free telephone call is placed (step 434). The triage operator 110 triages the caller (step 436). The triage process can result in an on-site resolution (step 438), wherein the caller 105 is given on-site treatment or instructions for self-care without visit to an off-site provider. There may be no Workers' Compensation claims (step 438) when the employee returns to work ("RTW") after being given medical information (step 442), when on-site self-care is provided (step 444), or when an alternative duty is assigned to the employee (step 446). With these dispositions (steps 442, 444, 446), the triage operator 110 follows up with the caller, as indicated by the relevant triage categories (step 448).

Alternatively, the caller 105 will be referred to a medical provider (step 440). This can happen for any of the following dispositions: Emergent-911 disposition (step 458), Emergent disposition (step 456), Urgent disposition (step 454), or Non-Urgent disposition (step 452), as determined by the instructions associated with each of these dispositions. Care is then transferred to the off-site provider (step 460) per the selected disposition.

The triage center can update the data warehouse and then notify the client organization of the particular injury and resolution (steps 450, 452). Work sites, regional offices, franchise offices, division offices, etc. can be the recipients of such a report, or receive other communications regarding the injury or issue. Each of those levels can have a particular interest in safety, human resources issues, Workers' Compensation issues, or other relevant issues. Likewise, a third-party administrator, insurance carrier, insurance broker, or other entity can be contacted when the client so requests (step 452). Ultimately, it is hoped that the employee returns to work (step 454).

Triage Categories

Within the triage system, different triage categories are applied based on the caller's complaints. The triage categories aggregate different types of supporting information and germane inquiries that apply to the particular conditions targeted by the categories. FIG. 8 shows a schematic representation of the various sections of an exemplary triage category 480: Critical Considerations 482, Clinical Frame 484, Tiered Triage Questions 486, Question Rationale 488, Self-Care 490 (including an overview, self-care instructions, prevention advice and follow-up questions), Frequently Asked Questions ("FAQ") 492 and General Information 494. An exemplary screen format for accessing these sections is described with regard to FIGS. 14E-F.

Any of these sections can be accessed at any time by opening up frames, or can be automatically presented to the triage operator 110 when a certain category 480 is called up. For example, one or more of the sections 482-494 could open as a frame automatically as soon as a particular category 480 is accessed, while others are available at the option of the triage operator, by selecting a button, drop-down menu or other selection modality. The categories do not necessarily have all of these sections, and can have additional sections not listed here.

The Critical Considerations 482 section generally guides the triage operator's questioning of the caller 105. The Critical Considerations 482 section can be used to flag important information or safety concerns for consideration during application of the tiered triage questions 486 and alert the triage operator 110 to other important information related to the tiered triage questions 486. For example, when the triage operator 110 decides to apply the abdominal injury triage category, the Critical Considerations 482 window appears on-screen before any questions are asked. The Critical Considerations 482 can alert the triage operator 110 to the fact that an abdominal injury can result in potentially life-threatening conditions, including the rupture of solid or hollow viscera and that an abdominal injury in a pregnant woman can result in uterine abruption or rupture. If this were not known by a triage operator 110, he or she might incorrectly discount the level of danger that the caller 105 faces. The software can automatically present the relevant Critical Consideration 482 on screen when the category 480 is selected, or it can be presented upon selection of an icon on the computer screen.

A Clinical Frame section 484 in a triage category 480 can be accessed by the triage operator. Unlike the Critical Considerations section 482, this section can be structured as a text box in which the triage operator 110 can type a short description of the mechanism, location and time of injury and any treatment attempted and corresponding results. A text box 662 for entering the clinical frame is shown in FIG. 14C. Alternatively, this section can actively request information, and such requests can be tailored to each triage category.

The Clinical Frame 484 can be important in determining the severity of the complaint. Answers to the questions provided in this section can help define the context for the injury or condition and alert the triage operator 110 to important issues, as well as any other categories that ought to be applied in a given inquiry. For example, symptoms resulting from a fall can be treated differently depending on whether the fall was from a 10-foot ladder or on level ground. A fall from a 10-foot ladder can alert the triage operator 110 to an increased potential severity of the condition and add to the list of, or cause the software to automatically access, applicable triage categories and/or dispositions.

One of the basic features of the triage category 480 is the tiered triage questions 486, which, when applied, can determine the disposition of the caller. The tiered triage questions 486 are discussed below, in reference to FIG. 9.

For each prompted question in the triage questions 486, the triage operator 110 can access the Question Rationale 488 section. The Question Rationale 488 section can help triage operators 110 understand the process and provide guidance for real world situations that do not fit neatly into tiered triage questions 486. This section can also be helpful for triage operators 110 who are in training or who are using a new triage category or a triage category with which they are not familiar.

The Self-Care section 490 provides category-specific self-care instructions to the caller 105 and a brief explanation of the condition, including measures the caller 105 might take to prevent a similar medical condition in the future. For example, the self-care instructions for the upper extremity injury category shown in FIG. 10 include: the administration of acetaminophen, aspirin, or ibuprofen; that the affected area be elevated; that ice and/or heat be applied to the affected area; and that work is modified to restrict lifting or forced grasp. This section 490 can include a list of symptoms that can develop and for which follow-up and reevaluation is necessary (i.e., "red flags"). For example, in the "bite wounds" triage category, any sign of infection or loss of sensation can suggest that the caller 105 should contact a medical provider immediately. The Self-Care section 490 can include general information about the category, discharge instruction, and a definition of all possible dispositions. This section can include both self-care as the ultimate treatment and interim self-care instructions which are applied in the time before a medical facility can be reached or other medical help arrives.

If the caller 105 asks questions about his condition, the triage operator 110 can choose to answer the questions using his or her own knowledge. In some cases, the triage operator 110 can find it helpful to refer to a Frequently Asked Questions section 492 of the triage category for a brief explanation of the medical condition and answers to common concerns. For example, those being triaged for animal bite wounds often ask if HIV can be transmitted to them as a result; the answer provided in the Frequently Asked Questions section 492 is that animals do not transmit HIV.

The General Information section 494 can contain additional information about the condition or information not suited for the other sections. For example, hyperlinks to Internet sites, Local Area Network, or other data sources containing more detailed medical information can be put in this section.

Tiered Triage Questions

Figure 9:
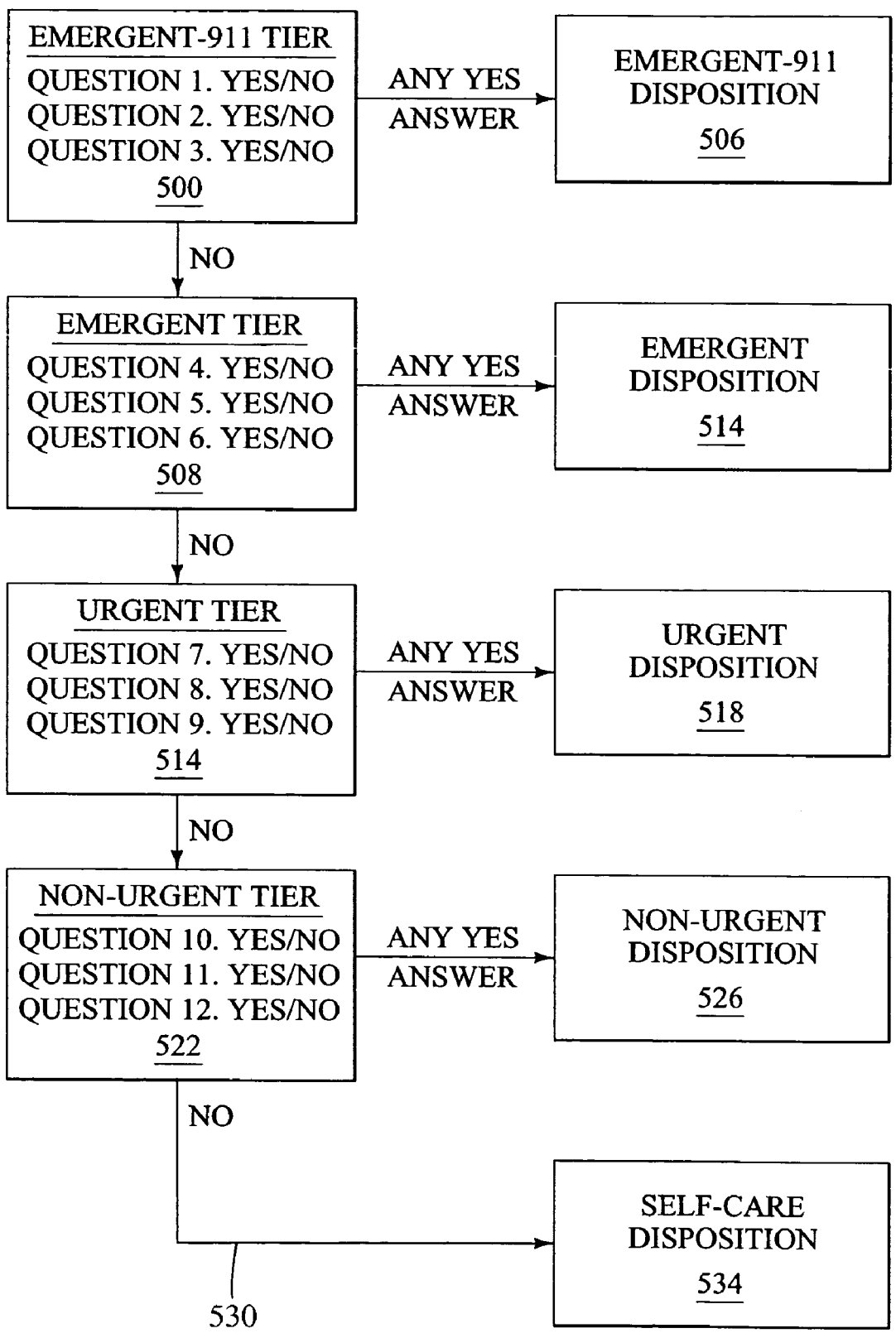
FIG. 9 is a schematic depiction of one set of tiered triage questions and corresponding dispositions.

As stated before, the triage questions can be tiered. That is, there are groups of questions in each tier and the tiers are ranked by urgency level. For each tier there is a corresponding disposition that is appropriate for the urgency level of the tier. An exemplary format of the tiered triage questions is shown in FIG. 9. Tiers 500, 508, 514, 522 are shown in FIG. 9. In this example, the highest urgency tier is the Emergent-911 tier 500. Each of the tiers can have a corresponding disposition 506, 514, 518, 526, as shown in FIG. 9. An exemplary screen format for displaying the tiered triage questions and accepting answer inputs from the triage operator 110 is shown in FIGS. 14D-F.

In the Emergent-911 tier 500, for example, there can be at least one yes/no question. If any of the questions are answered "yes," then the corresponding disposition for that caller 105 is the Emergent-911 disposition 506. The Emergent-911 disposition 506 can include instructions for immediate referral to an ER by the local EMS, and, like some of the other dispositions, can include condition-specific interim care instructions. The Emergent-911 disposition 506 can be modified to include other instructions. The Emergent-911 tier 500 can be designed so that it can select those callers 105 who need quick transport, severe pain relief and/or special emergency medical services, such as cardiac monitoring and defibrillation capability. Emergent-911 is typically the highest urgency disposition. Interim care instructions can be provided for all categories when triaging results in an Emergent-911 disposition 506, Emergent disposition 514, Urgent disposition 518 or Non-Urgent disposition 526.

If all of the questions of the Emergent-911 tier are answered "no," then the triage operator 110 moves to the Emergent tier 508. In the Emergent tier 508, there can also be a number of questions, for which any "yes" answer results in the corresponding Emergent disposition 514. An Emergent disposition 514 can indicate that there should be an immediate referral to a medical provider, but not by an EMS. However, if all of the questions in the Emergent tier are answered "no," then the triage operator 110 can move down to the Urgent tier 514.

If any of the Urgent tier 514 questions are answered "yes," then the Urgent disposition 518 is warranted. An Urgent disposition 518 can require a referral to a medical provider on the day of the complaint or within 24 hours. If all of the answers to the Urgent tier questions are "no," then the triage operator 110 should move to the Non-Urgent tier 522. Any "yes" answers to any of the Non-Urgent tier 522 questions should result in the selection of the Non-Urgent disposition 526, which can require a referral to a medical provider within three days of the complaint.

In the example shown in FIG. 9, if there is a "yes" answer for an Urgent tier question, all remaining questions can still be asked of the caller 105, including those in the Non-Urgent 522 or Self-Care tiers. This can be in contrast to a "yes" answer for an Emergent tier 508 or Emergent-911 tier 500 question, for which the entire triage process can be halted, and the disposition immediately implemented. The cut-off point in the triage process in which a disposition is selected but questions of a lesser urgency are still asked can be set at any particular tier.

The self-care disposition 534 can be automatically selected (530) if all of the answers to the preceding triage questions are "no." Thus, no tiered triage questions are shown in this particular example, and the self-care disposition functions as a catch-all for those who do not fit in the other tiers. Alternatively, there may be triage questions in a self-care tier in order to assist in customizing the self-care instructions for the caller's condition, or if there is a lower urgency tier, among other reasons. This Self-Care disposition 534 can require self-care that is distinguishable from interim self-care, discussed above. If there is an on-site triage operator 110, such as a nurse, this nurse can help implement the Self-Care disposition.

As shown in FIG. 9, the triage questions from higher urgency tiers can be asked before those of lower urgency. Within the "abdominal pain" category, for example, the question about shortness of breath is in the Emergent-911 tier and precedes the question about blood in the urine which is in the Emergent tier. There can be any number of questions in each tier. Whether a "yes" or "no" answer is provided, the triage operator 110 can record comments made by the caller 105 or the triage operator's observations or thoughts. In some situations, the triage questions can be answered by the triage operator 110 instead of the caller 105.

For consistency, the triage system can be designed, as shown in FIG. 9, so that any "yes" answer to a question within a specific tier (typically indicating the presence of particular symptoms) results in the selection of the disposition that corresponds to that tier. This ensures consistency and prevents error. The software can present the triage questions as a list, grouped according to tier, and each having yes and no buttons. The selection of a "yes" answer using a button or drop-down menu could immediately bring up a frame that contains the disposition information. However, it is not necessary to require "yes" answers for selecting a disposition; "no" answers and combinations of "yes" and "no" answers can result in the selection of a particular disposition. Similarly, qualitative or quantitative information given by the caller 105 can result in one of the possible dispositions, such as with the quantification tool described below. Any question that does not lead to a disposition can be excluded from any of the triage questions.

The questions can be symptom-based. That is, the questions can relate to what the caller 105 can sense. This can allow a quicker and more consistent disposition of the caller 105 because it does not require an attempt at quantification or objectivity. This can also be a requirement for selection of suitable triage questions. However, quantified details of the actual incident, if there was one, can also be used to determine a suitable disposition. The questions can also be history-based, that is, addressing family history (e.g., family history of heart disease), social history (e.g., whether or not the caller 105 ever smoked) and past history (e.g., whether the caller 105 has a history of heart disease).

One aspect of the triage system can include its flexibility. It can be beneficial to allow the triage operator 110 to revisit any of the questions to review the answers or associated comments. The triage operator 110 also has the ability to navigate between unanswered triage question groups within the same tier. Using a "Triage Navigator" screen, the triage operator 110 can jump directly to specific categories or specific tiers within the triage questions. The Triage Navigator can take the form of a drop-down list, or a pop-up window with links to the other categories, as shown in FIG. 14D. The system can also utilize the responses to questions in other triage categories if the same question appears again later in another triage category. The system can also determine and consider the variation in responses to the same or similar questions that are asked more than once during the triage process and, for example, alert the triage operator 110 to that fact.

FIG. 10 shows an exemplary triage category 480 for triaging upper extremity injuries including a set of triage questions. The elements of the category 480 can be displayed as shown, or elements or portions thereof can be presented by computer frames automatically or on command. The category 480 includes supporting information such as Critical Considerations 482 in addition to the tiered triage questions 486. The tiered triage questions 486 are set up similarly to those in FIG. 9, in that any "yes" answer indicates the presence of a symptom and leads to the selection of a corresponding disposition. There are four question tiers 500, 508, 514, 522 shown in FIG. 10. No questions are associated with the Self-Care disposition 534.

The triage questions 486 and categories 480 can be drafted and organized so that they satisfy a particular set of rules or so that they have a particular set of characteristics, including those rules and characteristics discussed above. Having the triage questions 486 and/or categories 480 standardized in this way throughout the triage system can help streamline the triage process and make the triage process more predictable and/or consistent for the triage operator 110 and the caller 105, thereby helping to ensure consistent results.

In an example of a set of rules, reflected in the triage category 480 of FIG. 10, the triage questions 486 and/or categories are symptom-based. The triage questions 486 are organized according to urgency. Applying the triage questions 486 results in one of five dispositions: Emergent-911, Emergent, Urgent, Non-Urgent or Self-Care, corresponding to each of the tiers 500, 508, 514, 522, 490. Emergent-911 referrals may be based on a caller's need for speed of transport by an EMS, pain relief and/or special emergency medical services, such as cardiac monitoring and defibrillation capability. Emergent referrals are immediate referrals to a medical provider when the user does not need the specialized services of EMS, but requires an immediate evaluation. An urgent referral is a referral to a medical provider within about two days of the disposition being selected. A Non-Urgent referral is a referral to a medical provider within several days of the disposition being selected. A Self-Care disposition includes providing self-care instructions to the caller 105 so that he can care for his illness or injury. Additional dispositions can be "interim self-care" which relates to providing information before an eventual visit to a medical provider and "report only" which can be appropriate when there is no need for any level of medical care but the call is still reported. These dispositions are discussed further with reference to FIG. 9.

Further describing an exemplary set of rules, the questions are answered "yes" or "no" and can be answered by the triage operator 110, and are not necessarily the answers given by the caller 105. Any questions that are not yes/no questions can be eliminated from the set of tiered triage questions. The rule set can require that "yes" answers always result in the selection of the corresponding disposition. The questions 486 are tiered such that the first group of questions leads to an Emergent-911 disposition, the second group of questions leads to an Emergent disposition, and so on. For example, the question about significant gross deformity, which, if positive, leads to an Emergent-911 disposition, precedes the question about swelling over joints, which, if positive, leads to an Emergent disposition. One of the dispositions is selected when all of the triage questions 486 are asked. Triage questions 486 that do not add to the disposition are not included in the category 480. A clinical frame 484 can be requested via a prompt, as described above, which can include information related to the time, place and mechanism of injury.

Multiple Relevant Triage Categories

Often, for a given inquiry, more than one category can apply. When dealing with multiple categories, the software can facilitate the presentation of all relevant categories on-screen, including the tiered triage questions and supporting information. Additionally, the software can prompt for answers to the highest urgency questions from all of the relevant categories before prompting for answers to the questions that are of a lower urgency. For example, a user can call with symptoms that, following a brief consultation, are categorized as "abdominal pain without injury" and "chest pain without injury." The software would ensure that all of the questions that result in an "Emergent-911" disposition from both the "abdominal pain without injury" and "chest pain without injury" categories are answered before moving on to the questions that result in an Emergent disposition. Although it could be possible to ask all of the abdominal pain questions before moving on to the chest pain questions, this may cause an unnecessary delay of a 911 call or other action if the subsequent triage of the chest pain resulted in a higher urgency disposition.

Figure 11A:
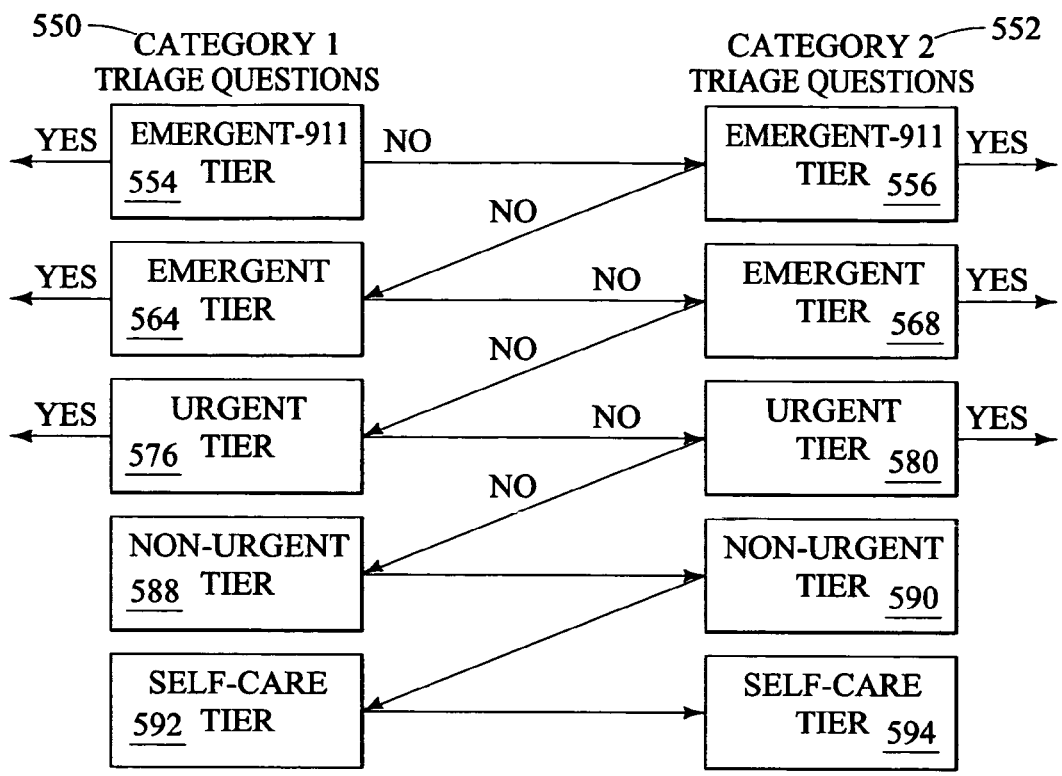
FIG. 11A shows a schematic depiction of a zigzag-type alternation between sets of triage questions.

One way of applying two sets of triage questions simultaneously is presented in FIG. 11A. This is termed a zigzag-type alternation. In the zigzag-type alternation, the questions in the Emergent-911 tier 544 from a first category 522 are asked, then the Emergent-911 questions 566 from the second category 522 are asked. Thereafter, the questioning returns to the first category 550, and the process is repeated at the next tier, as shown in FIG. 11A. Any "yes" answers for the Category 1 triage questions 550 can result in a selection of a corresponding disposition. Likewise, any "yes" answers, for the Category 2 triage questions 552 can result in a selection of a corresponding disposition. If "no" answers are given to all questions in the Emergent-911 and Emergent tiers, then the questions of the remaining tiers 576, 580, 588, 590, 592, 594 in both categories can be asked, without terminating the triage process at the first "yes" answer.

Figure 11B:
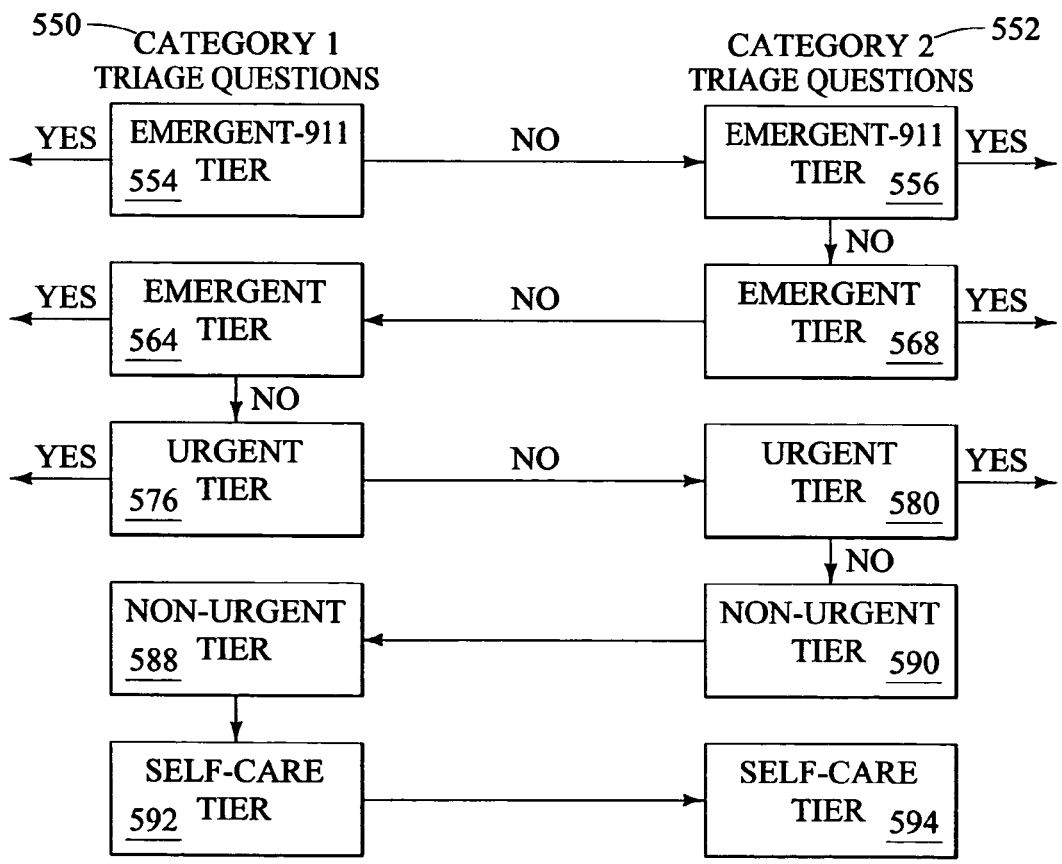
FIG. 11B is a schematic depiction of a step-type alternation between sets of triage questions.

FIG. 11B shows a step-type alternation for applying two sets of triage questions simultaneously. In FIG. 11B, the Emergent-911 questions are asked from a first triage category 550; then the Emergent-911 questions are asked from the second category 552. Instead of switching back to the first category 550, the triage operator 110 then asks the Emergent question 568 from the second category 552. Any "yes" answer for the Category 1 triage questions 550 can result in a selection of a corresponding disposition. Likewise, any "yes" answer for the Category 2 triage questions 552 can result in a selection of a corresponding disposition. If "no" answers are given to all questions in the Emergent-911 and Emergent tiers, then the questions of the remaining tiers 576, 580, 588, 590, 592, 594 in both categories can be asked, without terminating the triage process at the first "yes" answer.

The zigzag-type alternation depicted in FIG. 11A can be better for asking triage questions of two different categories when it is established that one of the categories is more important of the two. However, the scheme illustrated in FIG. 11B can be superior in some cases because there is less switching between different subject matters, thereby streamlining the flow of the conversation and minimizing the potential for either the caller 105 or triage operator 110 to become confused. However, regardless of the type of alternation scheme applied, the triage operator 110 can decide which category to apply first; this ordering can be more important in situations where there are more than two relevant categories and when the triage operator 110 suspects that a particular category or categories are more likely to yield a more urgent disposition.

In the course of conducting a triage, a triage operator 110 can determine that an additional triage category is warranted. It is not uncommon to discover information about the injury and its cause that leads the triage operator 110 to suspect additional, perhaps more severe, injuries. If the triage operator 110 determines that an additional category is relevant, the software allows him or her to apply the triage questions of that category at any time in the triage process.

For example, a triage for a "laceration" can reveal that the laceration extended into the eye. Thus, the "eye injury" category may need to be triaged along with the original laceration. Being able to immediately add the additional triage categories increases the likelihood that a more urgent disposition can be found sooner. Furthermore, the higher-priority questions of the after-added category can be posed to the caller 105 first before alternating between the two categories as shown in FIGS. 11A and 11B.

Figure 12:
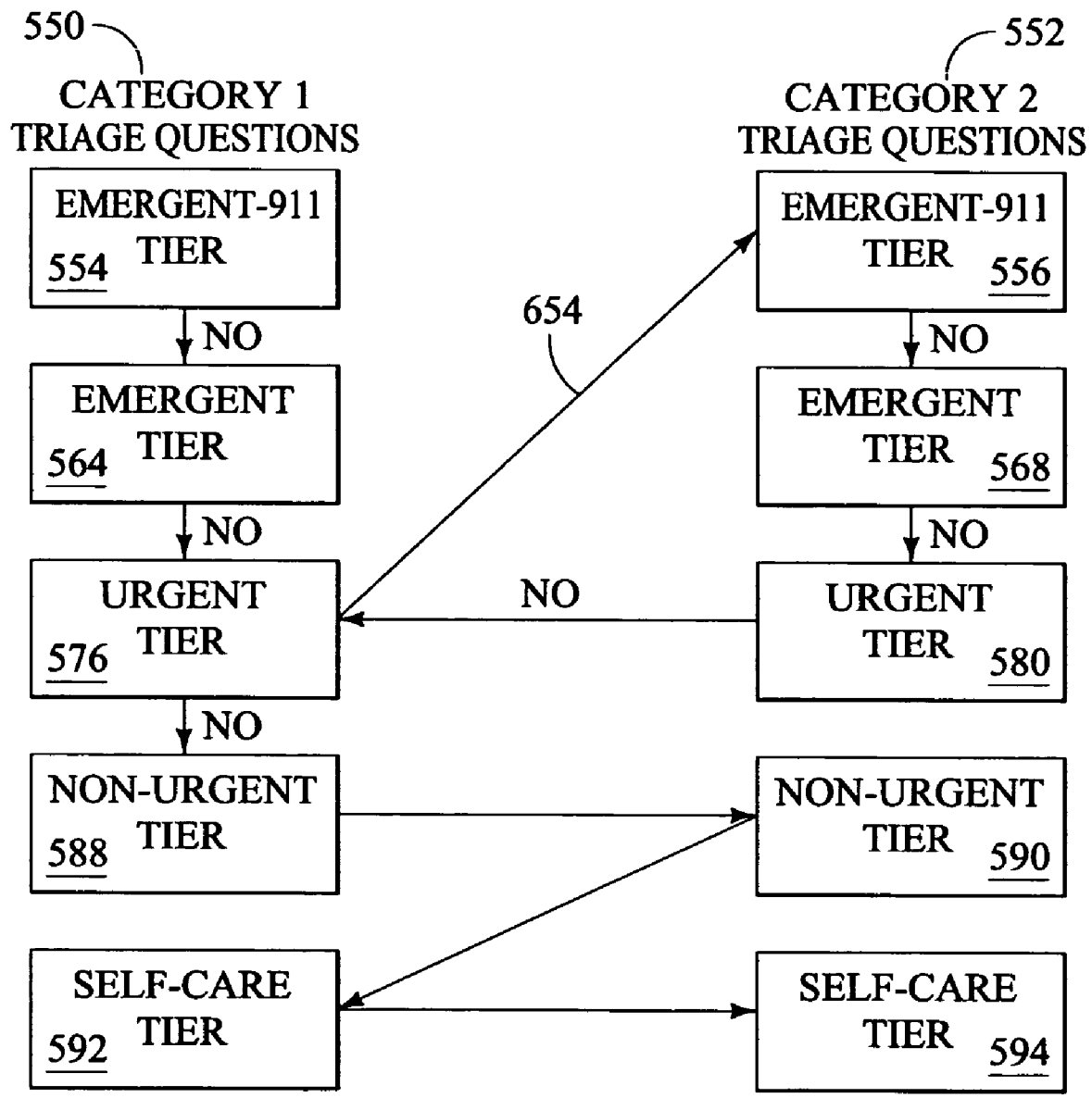
FIG. 12 is a schematic depiction of a method of alternating between triage questions in one triage category and another set of questions in a triage category added after triage was begun in the original category.

An example of a scheme for asking questions of after-added triage categories is shown in FIG. 12. As shown, the Emergent-911 (554) and Emergent questions 564 were asked of Category 1 (550), and "no" answers were offered to all of the yes/no questions in those two tiers. Then in the midst of the questions of the Urgent tier 576, it was discovered that a second category applies, so the triage operator 10 can immediately skip 654 to the Emergent-911 (556) questions of that new category, Category 2 (552). If all of the questions of the Emergent-911 tier 556 are "no" then the triage operator 10 continues to the Emergent tier questions 568. Again, if all of the answers are "no," the Urgent tier 580 questions can then be asked. At this point, if the Urgent tier 580 questions of Category 2 are all "no", then the triage operator 110 can continue with whatever Urgent tier 576 questions of Category 1 (550) have not been answered. If the answers to the Urgent tier 576 questions are "no," then the triage operator 110 can alternate between the remaining triage tiers 588, 590, 592, 594, as shown above. This can help ensure that any of the more urgent dispositions can be identified first before alternating between the lower-urgency tiers.

Record-Keeping, Reporting and Data Mining

The triage system can collect and store caller 105 data, including all data acquired during the triage process. The data is stored so that it can be selectively accessed for the purposes of record-keeping, reporting and data mining. Standard software reporting tools, such as BUSINESSOBJECTS 6.5 or subsequent versions (BusinessObjects, San Jose, Calif.), or the MedfilesMOL™ application described above can be used to access data that conforms to any of a variety of parameters, including dates, locations, individuals, company, corporate divisions, job type, age, etc. The record-keeping and reporting procedures can be customized to meet a client's specific needs, including by having reports tailored to particular state and/or industry requirements.

For example, the MedfilesMOL™ application can assist in Occupational Safety & Health Administration—("OSHA") and state-mandated record-keeping. This can include generating First Report of Injury and OSHA log updates. The application can identify recordable incidents by comparing injury type and treatments to OSHA's recording criteria. The MedfilesMOL™ application then tracks recordable cases and automatically updates the OSHA log. The client can be given partial access to a database so that a current OSHA log can be printed or viewed at any time, and, at year end, the OSHA-A summary can be generated.

The triage system can also improve the client's claim process system by providing more timely, accurate, complete and consistent reporting of injury incidents. The system can also collect and manage information with which to investigate and/or challenge, defend against, or settle such a claim.

Details about particular calls can be kept on file at the triage center 108 or elsewhere for auditing purposes. The triage software can automatically generate short narrative reports about each call or caller 105; these can be based on a pre-formatted report template. Reports, including narrative reports, can be automatically faxed, emailed, or otherwise communicated to the client or any interested division or entity listed above.

Users 210 can analyze the data to create reports, study injury trends, identify hazards, and compare one facility or department with another or with industry benchmarks, predetermined goals, or projected outcomes. The data gathered can also contribute to the maintenance of complete and accurate company records, accessible to authorized company personnel and/or others. Other reports can be automatically generated and sent to a company's safety officer, risk manager and/or insurance carrier to trigger accident investigation and preventive measures. The database of the system can be securely accessible to designated client managers via the Internet or other means so that the client can have access to these reports and other reporting options on demand. An exemplary computer screen format for accomplishing these reporting functions is shown in FIG. 14O.

Allowing the compilation and analysis of injury statistics can be helpful in situations where it is suspected that a small percentage of employees of a client can account for a large or disproportionate percentage of injury claims and costs. Users 210 can monitor particular callers 105 who use the triage system at higher rates and/or are more accident-prone. For example, the triage system can be designed to notify a user 210 when a certain caller 105 has reached a predetermined threshold for use of the triage system or injury rate.

The user 210 can mine the existing injury data to discover injury patterns or safety issues, including locations, job tasks, supervisors, or other criteria that may contribute to injuries. The system also allows users 210 to set injury threshold rates or other parameters for automatic notification via the system. The parameters can include a date range, site (e.g., "Store 315"), location (e.g., the loading dock), city and state, call type, caller gender, triage category applied, triage disposition, referral and/or treatment.

The user 210 can analyze the data to identify preventive measures, improve work safety rules and monitor compliance with work safety rules. For example, user 210 can assess whether any required safety equipment has an overall health or cost benefit. If the data reveal that wearing back-belts has no effect on back injury rates or costs over time, then client organizations can abandon the belts in favor of other preventative measures. Similarly, a manager can measure the rate of compliance with the safety measures. Customizing and automating this process can further help loss-prevention. The client can also monitor the performance of and cost-savings of the client's injury management service and the triage system itself.

The triage-related data can also be routinely mined to test the effectiveness of and fine-tune the instructions or other information dispensed by the triage operator 110. Various statistical methods can help pinpoint potential areas for improvement. This can help ensure optimal, evidence-based care. For example, if the follow-up for all callers 105 assigned to the Urgent disposition show unfavorable aggregate outcomes, the Emergent tier questions could be edited so that the Emergent tier captures a greater proportion of callers 105 or so that the questions better select those for whom that disposition is most appropriate. Triage questions and supporting information can be modified, supplemented or removed. Such undesirable outcomes can include both adverse health-related results of the applied disposition (e.g., when care is inadequate) and also when a level of care is excessive, resulting in unneeded expenditures. Alternatively, for example, the Urgent disposition could be modified, setting a smaller window of time in which to see a medical provider.

A threshold level of undesirable aggregate triage outcomes can be set. When the threshold level is exceeded, a user 210 can be alerted to modify the triage system to reduce the level of undesirable aggregate triage outcomes. Following any changes, the triage-related data can be again analyzed to determine the efficacy of any modification that was made to the system.

Additional Features of the Triage System

The triage system can be adapted to a client's specifications. The triage inquiry can be tailored to individual divisions, location of the incident, or job type. Likewise, the triage system can be specially configured for a particular U.S. state, call type, patient gender, category, disposition, referral, impression, and/or treatment. To accomplish this, the system can include, exclude or modify certain triage questions provided to the caller 105 or triage operator 110. Supporting information can also be included, excluded or modified. The particular client variations are identified and accessed as the caller 105 is identified. These variations can also be keyed to the place or business from which the caller 105 is calling. The triage system can, for example, suppress any data from being collected.

In a triage center, there can be triage operators answering the telephones and performing triage, and, in addition, a manager who monitors the center. An additional feature of the triage system can be a "Flag Review" button, which allows the triage operator 110 to flag a call for review by a manager. The "Flag Review" button can be used to identify a problem with the caller 105 or the way the triage category functions during the call. It can be used for immediate assistance, or for identifying possible areas for long-term improvements.

The triage system can allow for different types of system overrides. One kind of override is the 911 Override, which allows the triage operator 110 to immediately bypass the remaining triage process and call 911 or direct the caller 105 or the caller's supervisor to call 911. If the triage operator 110 feels the caller's condition has become dangerous and requires EMS dispatch, clicking this button by-passes triage and expedites the 911 referral. The 911 Override can be employed at any time in the triage process. The 911 Override can be accessed by a single button that is always present on the computer screen. The user can see a pop-up screen requesting entry of a caller's name, and a call-back telephone number.

Another kind of override, Triage Operator Override ("TO Override"), allows a triage operator 110 the ability to immediately bypass the remaining triaging of a caller. This TO Override feature also allows the triage operator 110 to automatically navigate to the Provider Search (Referral) screen at any point during the call flow. This allows the triage operator 110 to use his own discretion and professional judgment to, if desired, substitute a disposition that he feels is more prudent than that provided by the triage system. While a computerized triage system provides a valuable framework for triage, it is recognized that the software cannot anticipate the infinite number of variables and situations that a triage operator 110 can face. The TO Override feature helps the triage operator 110 address a situation in which he believes there is a more logical, safe or appropriate response than what the software has indicated. TO Override can also be used when, for example, the triage disposition is Self-Care, but the caller 105 insists on a referral. Selection of the TO Override feature can prompt the display of the Provider Search (i.e., Referral) screen.

A system override can prompt the triage operator 110 to provide the reason for the override and flag the call for manager review. The reason for the override can be indicated in an electronic record linked to the call record, but can be excluded from reports to the client organizations or government agencies, consistent with applicable laws and agreements with clients.

With some conditions, it can be important to obtain from the caller 105 quantitative details about the symptoms or cause of the ailment. Quantification tools supported by the software can be used by the triage operator 110 to quantify symptoms. Quantification tools can deal with the extent of bleeding, the amount of pain, shortness of breath, extent of burns, time of a possible rabies-infecting bite, and tetanus status. A quantification tool can, for example, help the triage operator 110 decide if bleeding can be considered "severe" bleeding. FIG. 13 shows an exemplary quantification tool 597 for determining whether a wound is deep or not. The triage operator 110 can ask some of the questions 598 within the quantification tool 597 and thereby choose the proper yes/no conclusion 598 about the wound depth. An icon can appear to the left of any triage question involving one of these symptom patterns, and can open a document with quantifying information to aid in answering the accompanying question. The information can assist in the selection of triage categories or selection of a disposition within a triage category. The quantification tools also provide standardization between the triage operators so triage results are consistent.

The time elapsed between an injury and the time the injured person contacts the triage operator 110 can be a factor in the triage analysis. For example, if a caller 105 is concerned about the possibility of a broken bone, a call immediately after the incident may not reveal some of the more important symptoms—whether there is swelling or bruising, for example. Therefore, the system can alert the triage operator 110 to the elapsed time and its relevance, modify questions based on the elapsed time (including eliminating questions that would not have relevance at a particular time and/or automatically adding others), have questions automatically answered in certain ways based on the time elapsed and indicate whether it is important for the caller 105 to follow-up at a later time. The elapsed time can otherwise be used to determine a disposition, such as, for example, when the incident was so long ago that nothing more than self-care is needed. The system can also make note of what time the event occurred in the caller's time zone, which will then be adjusted for a correct calculation of the elapsed time. This information can become part of the recorded triage-related data and stored in the database with the answers to the triage questions.

Screen Formats and Selection Modalities

Figure 14A:
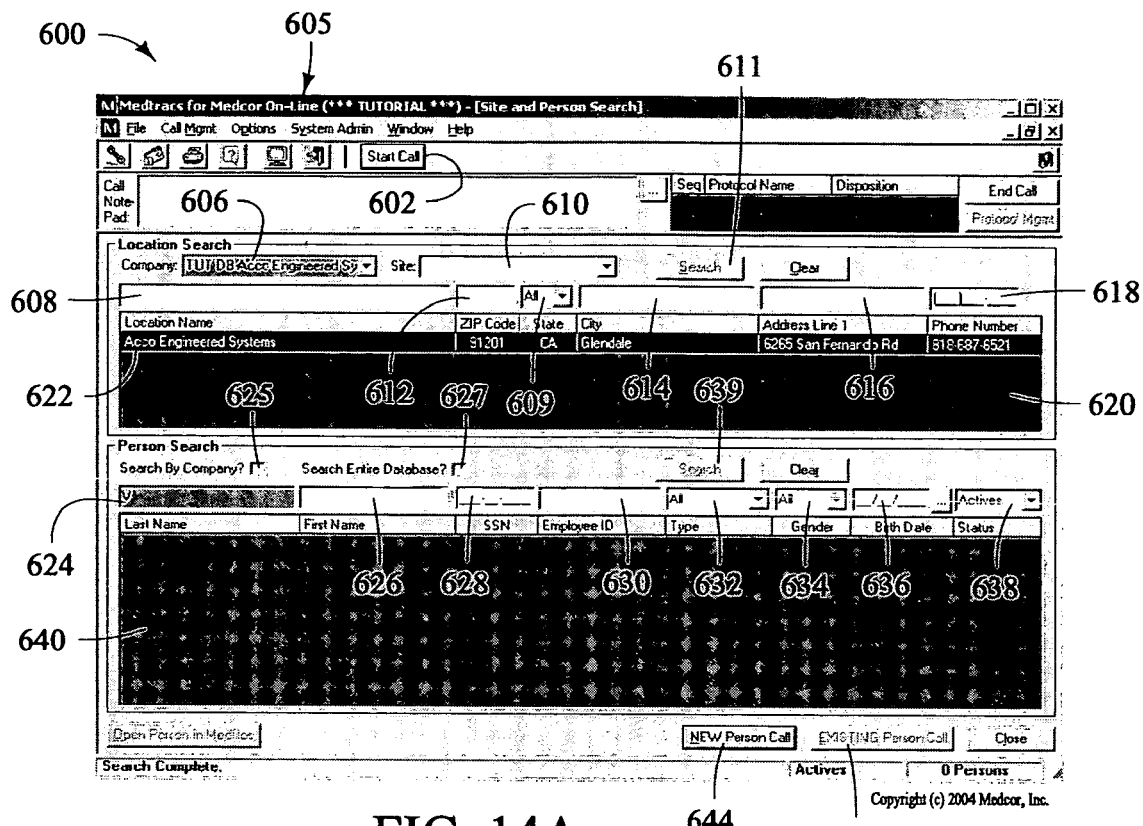
FIGS. 14A-P show various exemplary screen formats for implementing a triage system on a computer.

FIGS. 14A-P show various exemplary computer screen formats and selection modalities that can be used to help implement the triage system on a computer.

FIG. 14A shows a screen 600 that enables the identification of the caller 105 so that the triage-related data, including any information related to triage outcomes, can be associated with his demographic or personal information and so that client preferences can be applied to the call. When the triage operator 110 answers the call from the caller 105, the triage operator 110 can select the "Start Call" button 602, which can time-stamp the phone call and enable the triage system to be implemented. A menu bar 605 allows for selection of various actions and parameters, including exiting the program and changing program options.

As described above, the triage system can be implemented for a corporate client. Thus, the caller 105, if he is an employee, can be asked to identify the company for which he works, including the particular site, or where he is located. The company can be selected using a combo-box field 606, and the site can be selected using another combo-box field 610. As an alternative, search fields can be filled out, such as company 608, zip code 602, state 609, city 614, address 616 and phone number 618. Once selected fields are entered, the "Search" button 611 can be selected to generate a list of matching companies 622 in the company field 620. If one of the matching companies 622 is the correct one, it can be selected by double-clicking or other selection method.

The caller 105 can be asked if he is already in the database; if he is, the "Existing Person Call" button 604 is selected and the information about the caller 105 is accessed. Any number of search fields can be filled out to search for the relevant demographic data, including last name 624, first name 626, social security number 630, type of employee 632, gender 634, birth date 636, and job status 638. The entire database can be searched by checking the appropriate box 627, or the search can be restricted to a particular company by checking a different box 625. Once one or more fields are entered, the triage operator 110 can select the "Search" button 639, which brings the various matching identities into the person field 640, where the corresponding identity can be selected.

Figure 14B:
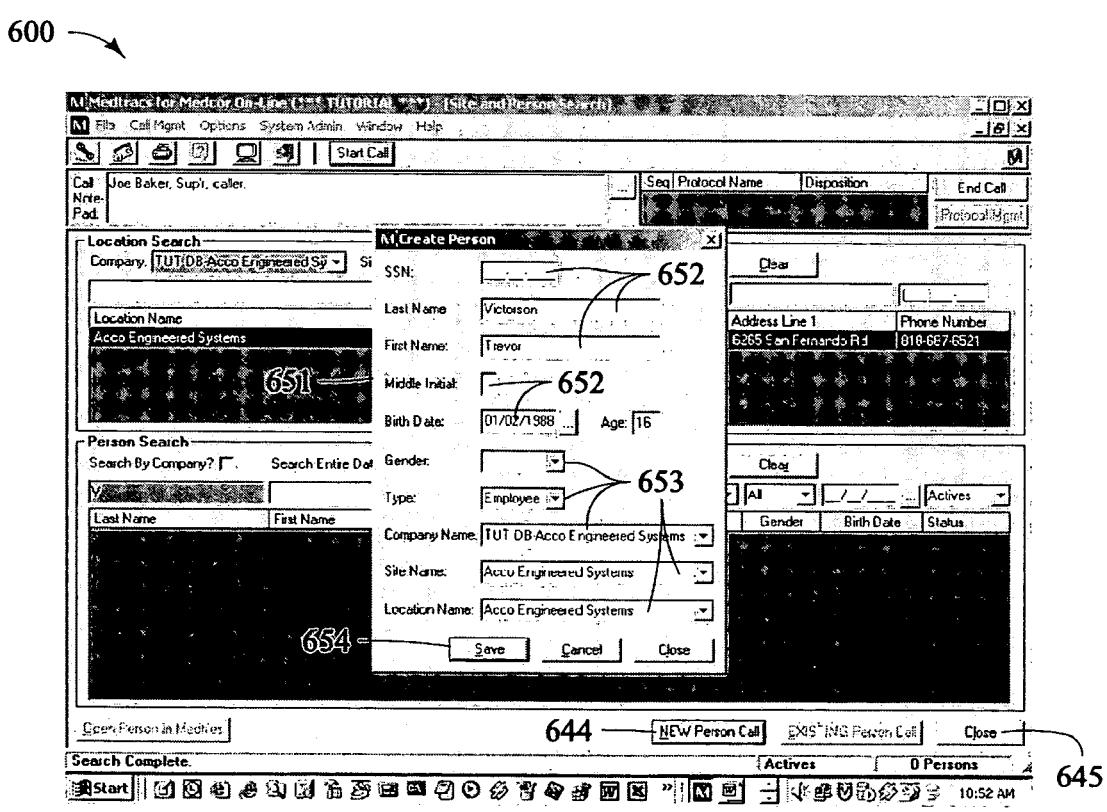
Figure 14C:
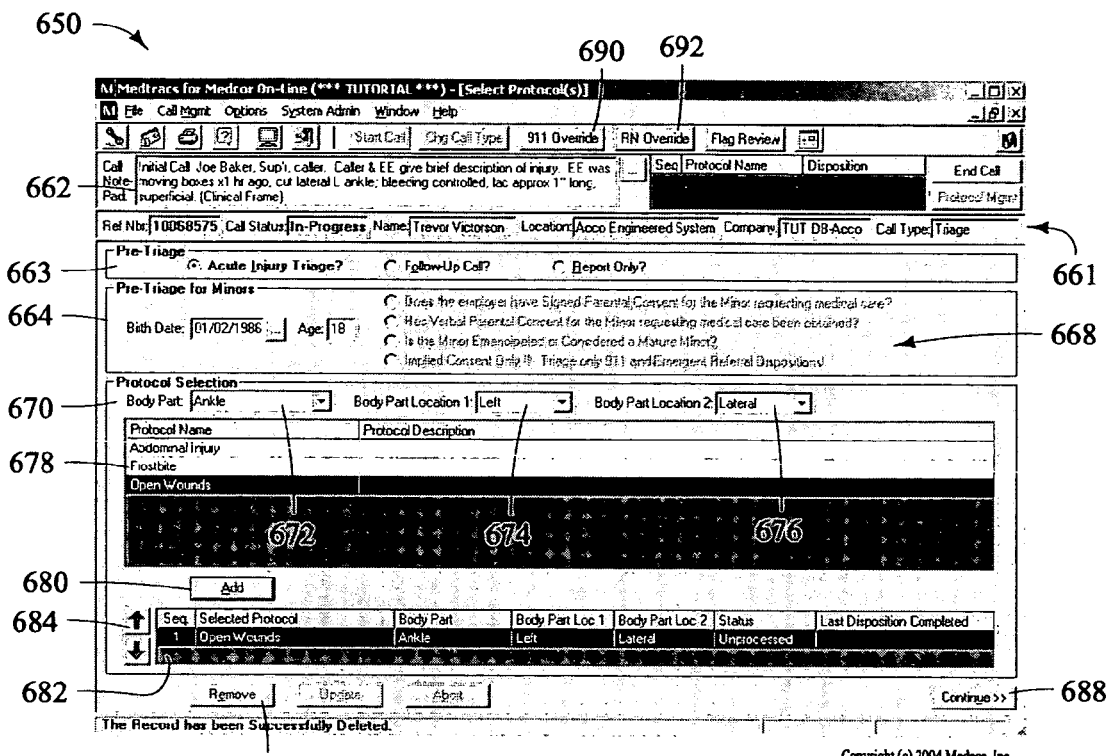
Figure 14D:
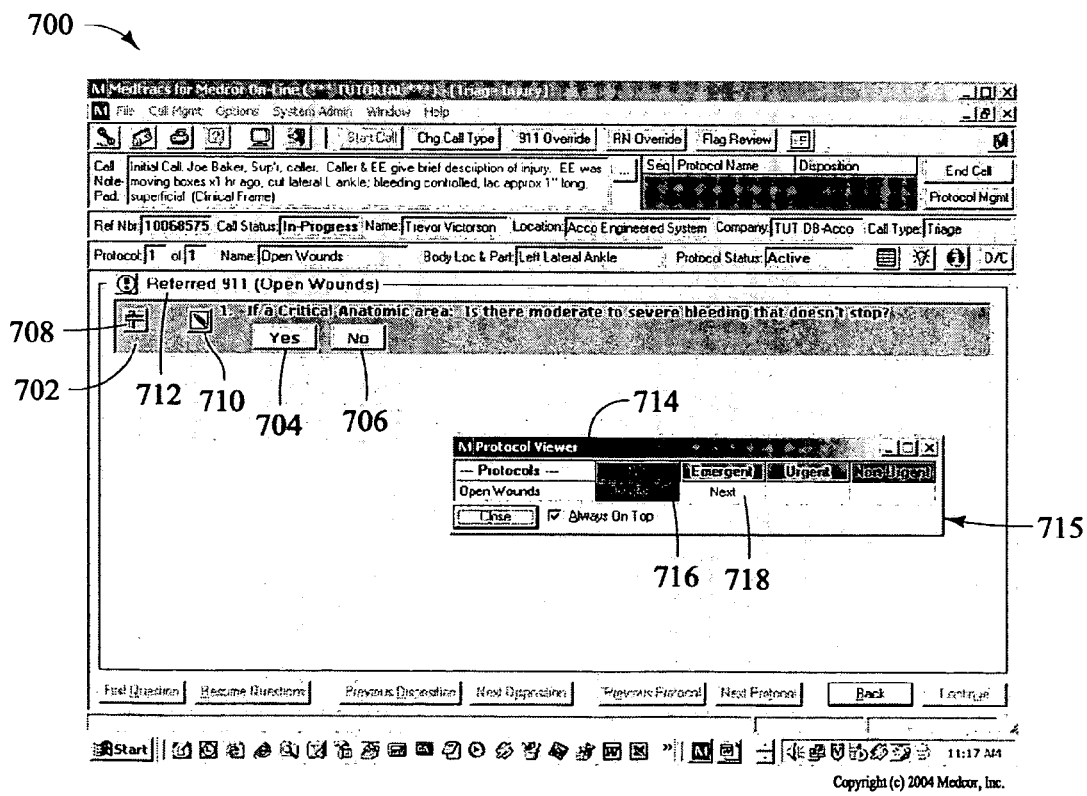
Figure 14E:
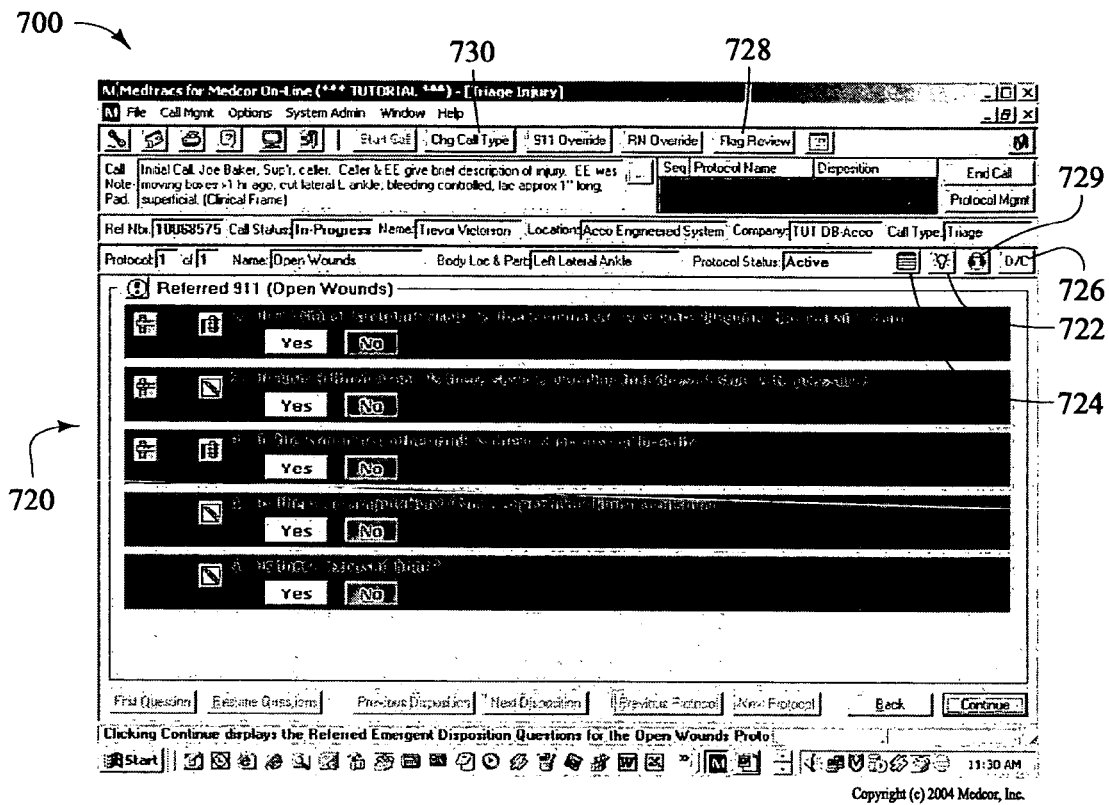
Figure 14F:
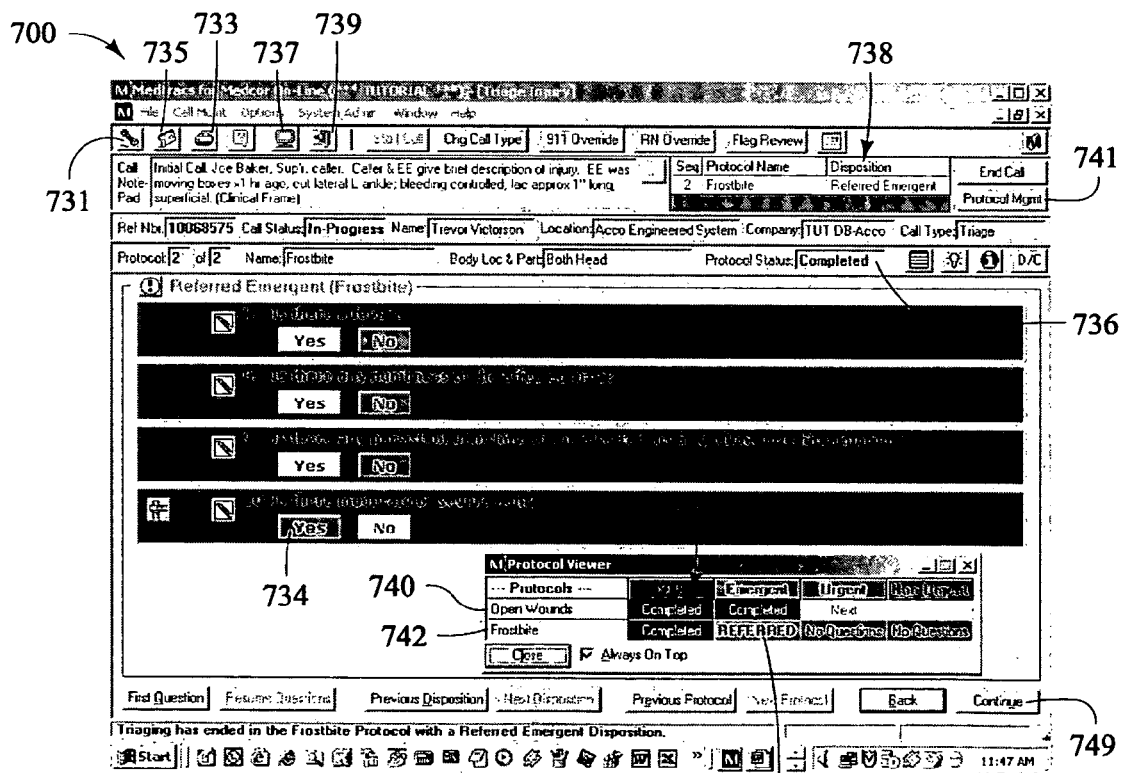

As shown in FIG. 14B, if the caller 105 is not in the system, the "New Person Call" button 644 is selected, and, as a result, the "Create Person" dialog box appears, having text fields 652 and combo-box fields 653, for entering demographic information such as birth date, social security number, gender, etc. Once all of the information is entered, the information can be saved by selecting the "Save" button 654, at which point the "Create Person" dialog box 651 disappears.

By selecting the "Close" button 645, the next screen 650 appears, in which the relevant triage categories can be selected, as shown in FIG. 14C. While the text box 662 can be used for any relevant information, it can also be used to enter the answers that the caller 105 provides for the introductory questions regarding the context or mechanism of injury, which can be a first step in the selection of the relevant triage category. The initial questioning can also help determine if the call is an injury, follow-up or report-only call, which can be selected using the radio buttons 663. Toward the beginning of the call, the triage operator 110 can request the age of the caller 105. If a birthday entered in the age box 664 indicates that the caller 105 is a minor, then the triage operator 110 can select one of the legal consent categories 668 described above in order to proceed. The system can prevent the triage operator 110 from proceeding if there is no indication of consent, although this feature can be disabled. An information bar 661 is visible throughout the call, indicating the name of the caller 105, as well as the name and location of the company for which the caller 105 works, the reference number for the call and the call type.

The triage categories can be selected in category selection box 670 of FIG. 14C from the list of categories 678. To apply the chosen category, the applicable information is selected using combo-boxes corresponding to body parts 672, body part location 1 (674) and body part location 2 (676). The body part location combo-boxes include such descriptors as dorsal, lateral, anterior, posterior, left, right, etc. Once these have been selected, the "Add" button 680 is selected, which saves the selected combination in the relevant triage category list 682. This process can be repeated using different categories and/or different body parts until there are no more relevant categories for the caller's particular condition. Using the arrows 684, a plurality of categories can be ordered in terms of importance or other criteria. Selected categories can also be removed using the "Remove" button 686. Also, the "911-Override" button 690 and the "Triage Operator Override" button 692 can be selected throughout the triage process. Once the selection process is finished, the triage operator 110 can select the "Continue" button 688 to move to the screen of FIG. 14D.

The screen 700 of FIG. 14D starts the triage questioning based on the categories selected in the previous screen 650. The triage questioning starts with the questions in the highest urgency tier of the highest priority category, which are identified by the question identification 712 bar. The Triage Navigator 714 shows which tier of questions is currently being asked 716 and which tier of questions is next 718, based on the tier list 715. When asking the triage questions, the triage operator 110 can access the quantification tool 708 which displays a methodology for quantifying certain symptoms. The triage operator 110 can also select the button 710 to open a text box that allows the entry of additional information acquired from the caller 105 in the course of answering a particular question.

As stated above, the Critical Considerations section can be accessed throughout the triage process. In the screen shown in FIG. 14E, this section can be selected using the "Critical Considerations" button 722, which opens a window containing the relevant information. Some additional features that can be available through the triage process are the "Change Call Type" button 730 (for alternating between a follow-up call, new call and report-only call), the "D/C" button 726 (for accessing self-care instructions and FAQs), the "Triage Navigator" button 724, the "General Information" button 729 and the "Flag Review" button 728, which are all discussed above. Furthermore, there are buttons for accessing a prior call menu 731, accessing a list of outgoing follow-up calls to be made 733, printing the screen 735, closing all screens 737 and exiting the program 739. The "Protocol Management" (i.e., Category Selection) button 741 allows the triage operator 110 to return to the screen 650 shown in FIG. 14C to select additional categories or to change categories.

The triage screen 700 of FIG. 14F shows multiple triage categories being applied. In particular, FIG. 14F shows Open Wounds 740 and Frostbite 742, as indicated in the Triage Navigator 744. The Triage Navigator can be used to view any of the completed or active tiers in any of the selected categories. Because one of the questions has been given a "yes" answer 734, the Disposition box 738 shows the selected disposition and the Triage Navigator 744 shows that the caller 105 has been referred 748. Because the disposition is Emergent, the triage status box 736 shows that the triage process has been completed; if, however, the selected disposition was of a less urgent nature, the protocol status box 736 may not show that the triage process has been completed until all of the triage questions in all tiers have been asked, as described above. The "Continue" button 749 can be selected to move to the next screen.

Figure 14G:
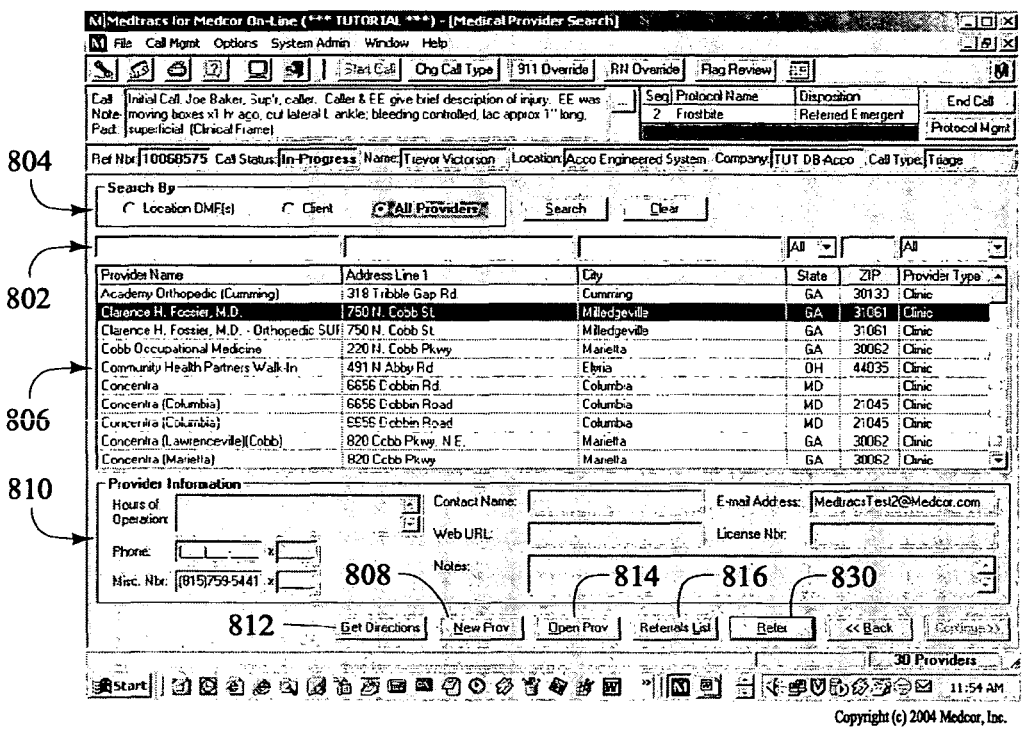

The screen 800, shown in FIG. 14G, allows the triage operator 110 to find an appropriate medical provider, and offers a number of different search modes. For example, the search can be restricted to designated medical facilities, client specifications, or can be expanded to all providers using a number of radio buttons 804. Alternatively, any number of fields 802 can be filled to search the provider database. The results of the search show up in a list 806. Details about the medical provider can be obtained by selecting the "Open Prov" button 814 which opens a text window. The "Referrals List" button 816 can be selected to obtain the referrals for a particular medical provider. Directions to a provider can be obtained by selecting the "Get Directions" button 812, which can access a map or directions from any appropriate service or software, such as MAPQUEST.COM. If a medical provider is not in the database, the medical provider can be entered by selecting the "New Provider" button 808 and entering the new provider fields 810.

Figure 14H:
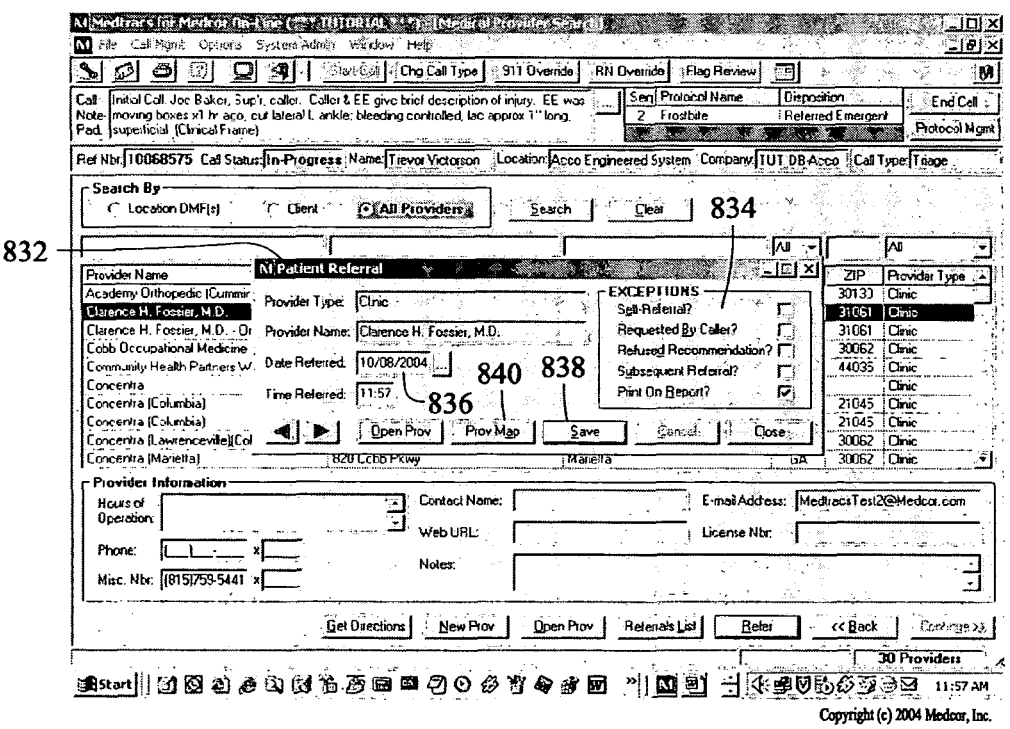
Figure 14I:
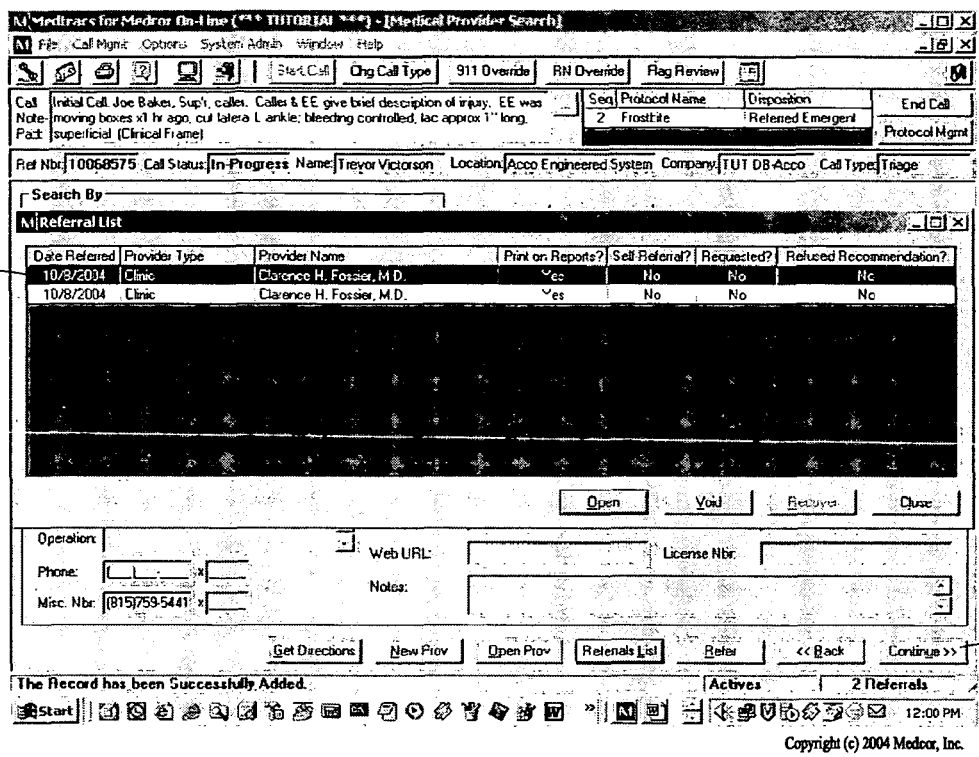
Figure 14J:
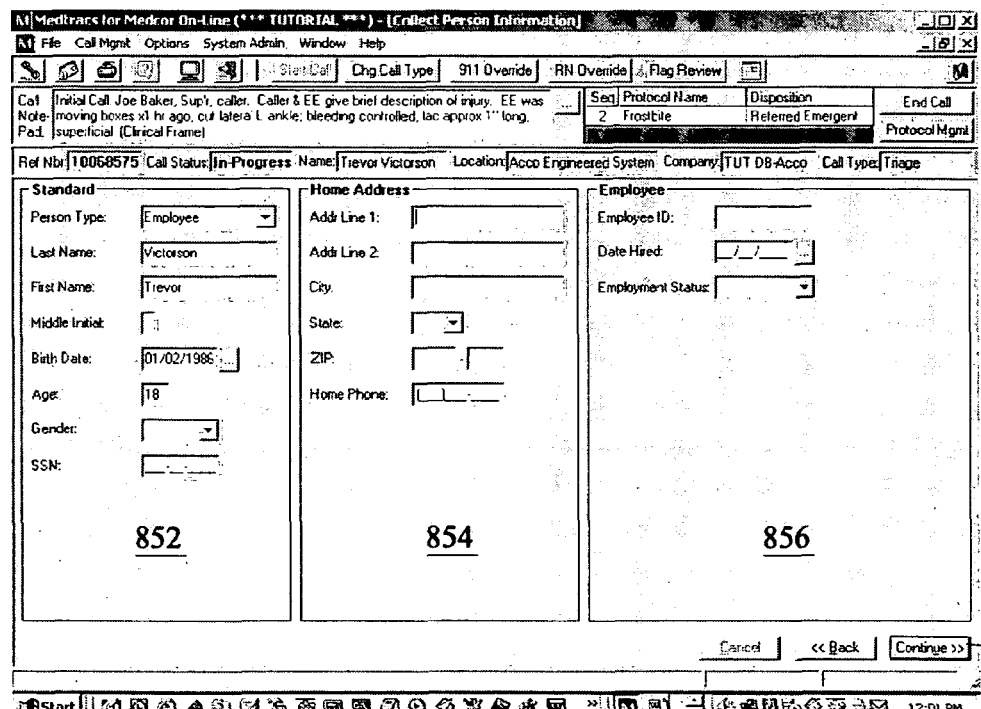

Once a medical provider has been selected, the "Refer" button 830 is selected, which opens the caller referral window 832, shown in FIG. 14H. The caller referral window 832 summarizes the referral by providing the date of referral 836 and other information. A button 840 can also allow a map to the medical provider to be generated. A number of details about the nature of the referral can be selected; these are indicated as Exceptions 834 to an ordinary call, and include such details as whether there was a self-referral by the caller 105, whether the caller 105 requested an appointment, refused a recommendation, etc. The Exceptions 834 also allows the referral information to be printed on the medical report.

Once the "Save" button 838 is selected, the information is saved in a record 842, and the triage operator 110 can select the "Continue" button 844 to move to the next screen 850, shown in FIG. 14J. Further demographic information can be acquired, such as personal information 852, home address 854 and employment data 856. The "Continue" button 858 can be selected to move to the next screen 900, shown in FIG. 14K.

Figure 14K:
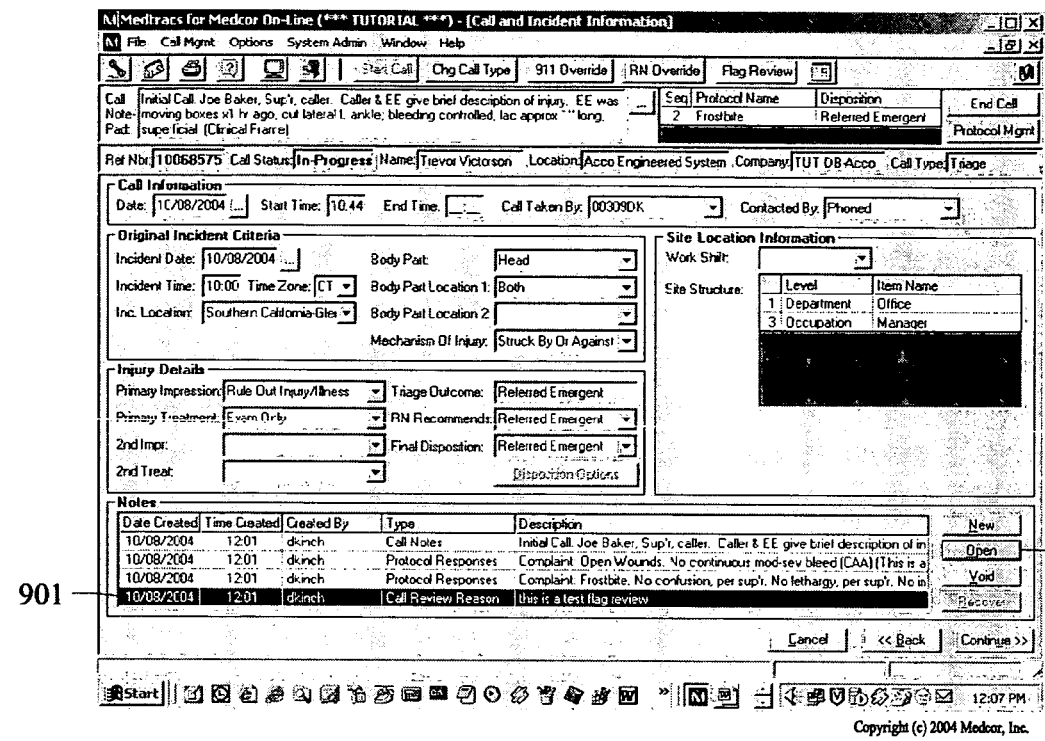
Figure 14L:
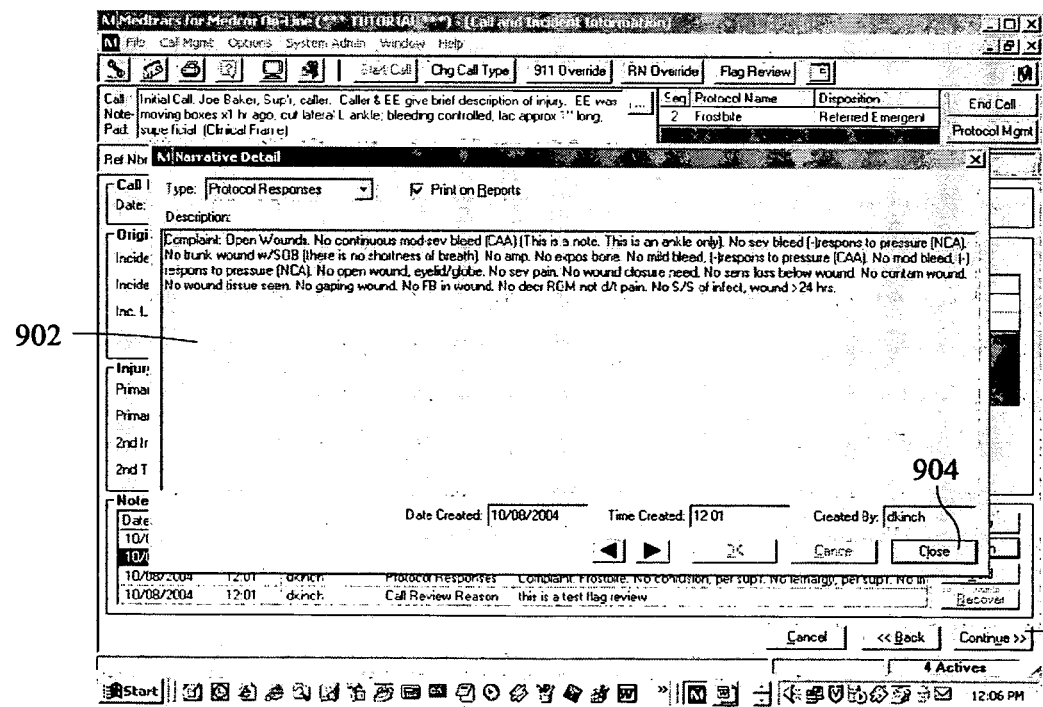
Figures 14M, 14N:
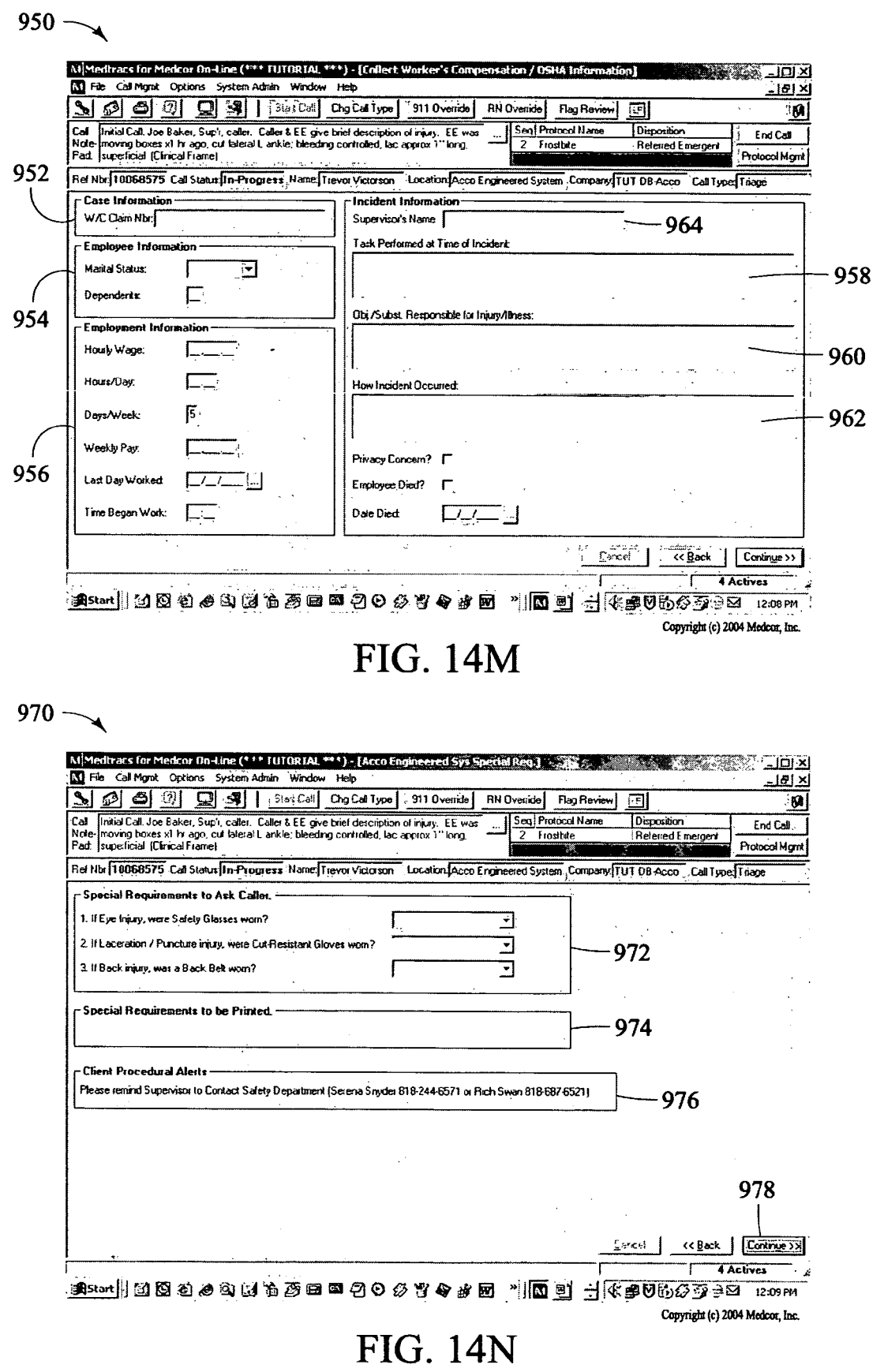
Figures 14O, 14P:
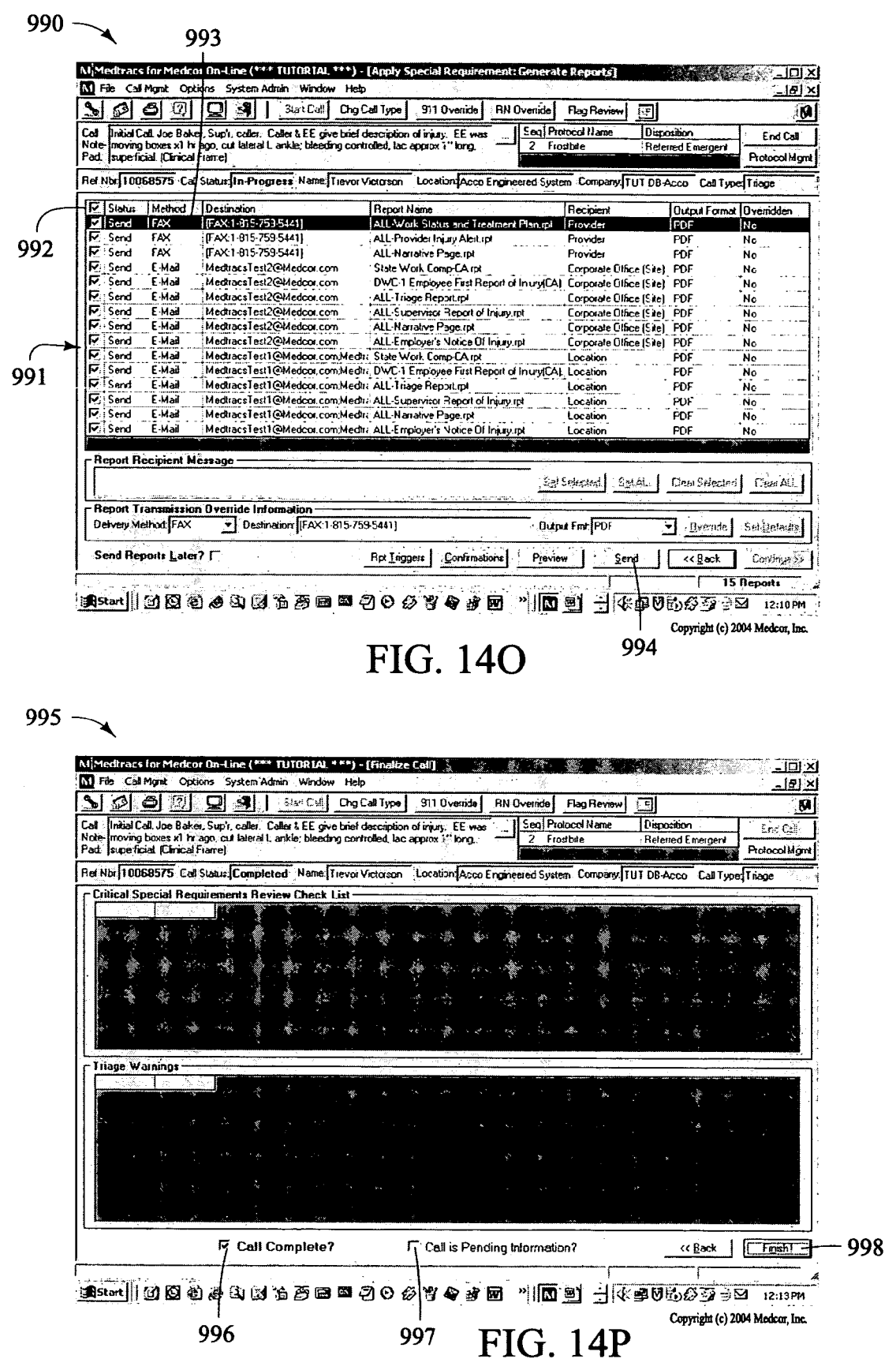

When a particular call is selected from the call list 901, a summary of that call is displayed in the various fields of a screen 900 shown in FIG. 14K when the "Open" button 903 is selected, a narrative description 902 of the call is generated and displayed, as shown in FIG. 14L. The narrative description can be closed using the "Close" button 904, and the next screen 950 can be accessed using the "Continue" button 906.

The screen 950 shown in FIG. 14M allows additional demographic information to be entered, including a Workers' Compensation Claim Number 952, family information 954, employment information 956, and contextual information relating to the incident itself, including the task performed at the time of incident 958, the objects or substances involved 960, the details about the occurrence of the injury 962, and the supervisor's name 964. After this information is input, the next screen 970, shown in FIG. 14N, permits the recording of information specific to the employer of the caller 105, such as compliance with particular safety procedures 972. Some of these special requirements can be printed, and if printed, will show up in a text box 974. Additional text 976 can alert the triage operator 110 to any other details particular to the caller's employer. When this information is entered, the "Continue" button 978 is selected to access the next screen 990.

The next screen 990, shown in FIG. 14O, displays the details of the automated communications 991 that will be sent on command, including the destination, the report name, the recipient, and the output format. The list of communications can be selected or deselected using check-boxes 992. The method 993 of the communication can include e-mail and fax, but all other communication methods described above can be employed. Once the selections are made, the "Send" button 994 is selected. In FIG. 14P, the final screen 995 is shown. The Call Complete 996 or Call Pending Information 997 boxes can be checked, after which the "Finish" button 998 is selected to complete the call.

While various embodiments of the triage system have been described, it will be apparent to those of ordinary skill in the art that many more embodiments and implementations are possible within the scope of the triage system. Accordingly, the triage system is not to be restricted except in light of the attached claims and their equivalents.

The invention claimed is:

1. A computer-implemented, triage category method for determining a medical triage disposition, the method executed by a computer including a processor and coupled with storage, the method comprising:
   providing, by the computer to a triage operator, a set of tiered triage questions consisting of a plurality of only yes/no questions arranged in a plurality of tiers, wherein the plurality of tiers are ranked according to a level of urgency;
   providing, by the computer to the triage operator, a plurality of dispositions corresponding to the plurality of tiers, wherein a first "yes" answer received in response to any of the plurality of only yes/no questions directly results in selection by the computer of a disposition that corresponds to the tier which contains the affirmatively-answered question, wherein triage dispositions are final determinations whether and to what level of medical care a person undergoing triage is directed, the plurality of only yes/no questions and the plurality of dispositions designed to allow inquiry of the person by the triage operator when the person is located remotely from the triage operator; and
   storing the plurality of only yes/no questions in relation to the corresponding plurality of dispositions in a database within the storage of the computer.

2. The method of claim 1, wherein one of the triage category and the set of tiered triage questions is developed in accordance with a rule set.

3. The method of claim 2, wherein the rule set improves triage consistency.

4. The method of claim 1, wherein one of the triage category and the plurality of only yes/no questions is symptom-based, or based on something the person can sense.

5. The method of claim 1, wherein the plurality of only yes/no questions are answered in the computer by the triage operator.

6. The method of claim 1, further comprising:
   providing clinical frame inquiries related to a time of injury, a place of injury and a mechanism of injury.

7. The method of claim 1, wherein the plurality of dispositions comprise:
   emergent-911 transport by an emergency medical service to a medical provider;
   emergent referral immediately to a medical provider;
   urgent referral to a medical provider within about two days of the disposition being selected;
   non-urgent referral to a medical provider within several days of the disposition being selected; and
   self-care instructions.

8. The method of claim 7, further comprising:
   providing interim self-care instructions to the person in anticipation of an eventual visit to a medical provider; and
   only reporting a call when no medical care is determined to be necessary.

9. The method of claim 1, further comprising:
providing triage to the person remotely, away from a treatment center or without access to medical equipment or a person with medical training, through a form of remote communication.

10. The method of claim 1, further comprising:
providing to the triage operator a plurality of additional questions to quantify responses to at least some of the plurality of yes/no questions so as to properly interpret the response as a "yes" or a "no."

11. A computer-implemented method of developing a set of standardized triage categories for organizing medical triage inquiries, the method executed by a computer including a processor and coupled with storage, the method comprising:
providing, to the computer, a plurality of triage categories comprising body parts, injury types, symptoms, or a combination thereof;
providing, to the computer, a plurality of tiers within each of the plurality of triage categories, wherein the plurality of tiers are ranked according to urgency level by the computer, and wherein each of the plurality of tiers corresponds to one of a plurality of different triage dispositions, wherein triage dispositions are final determinations whether and to what level of medical care a person undergoing triage is directed;
sorting with the computer only yes/no questions into the plurality of triage categories, wherein the computer sorts the questions into the plurality of tiers based on a correlation that each of the questions has with the urgency level of each of the plurality of tiers;
wherein a "yes" answer to one of the questions indicates the presence of a symptom or a visible injury related to a medical condition and a "no" answer to one of the questions indicates the absence of the symptom or the visible injury related to the medical condition, wherein a first "yes" answer received in response to any of the questions asked by a triage operator directly results in selection of a disposition that corresponds to the tier which contains the affirmatively-answered question except within either of a non-urgent and self-care tier, the questions and the plurality of dispositions designed to allow inquiry of the person by the triage operator when the person is located remotely from the triage operator; and
storing, by the computer, the questions in relation to the corresponding plurality of dispositions in a database within the storage of the computer.

12. The method of claim 11, wherein the plurality of triage dispositions comprise:
emergent-911 transport by an emergency medical service to a medical provider;
emergent referral immediately to a medical provider;
urgent referral to a medical provider within about two days of the disposition being selected;
non-urgent referral to a medical provider within several days of the disposition being selected; and
self-care instructions.

13. The method of claim 12, further comprising:
providing interim self-care instructions to the person in anticipation of an eventual visit to a medical provider; and
only reporting a call when no medical care is determined to be necessary.

14. The method of claim 11, wherein the only yes/no questions are developed in accordance with a rule set.

15. The method of claim 14, wherein the rule set improves triage consistency.

16. The method of claim 11, wherein the only yes/no questions are answered in the computer by the triage operator.

17. The method of claim 11, further comprising:
providing clinical frame inquiries related to at least one of a time of injury, a place of injury and a mechanism of injury.

18. The method of claim 11, wherein one of the plurality of triage categories and the only yes/no questions is symptom based, or based on something the person can sense.

19. The method of claim 11, further comprising:
providing triage to the person remotely, away from a treatment center or without access to medical equipment or a person with medical training, through a form of remote communication.

20. The method of claim 11, further comprising:
providing a plurality of additional questions to quantify responses to at least some of the yes/no questions so as to properly interpret the response as a "yes" or a "no."

21. A computer-implemented method of determining tiered triage questions for a triage category, the method executed by a computer including a processor and coupled with storage, the method comprising:
identifying, by the computer being operated by a triage operator, a relevant category of triage comprising body parts, injury types, symptoms, or a combination thereof applicable to a person undergoing triage;
providing, by the computer to the triage operator, a plurality questions consisting of only yes/no questions, wherein a "yes" answer to one of the questions indicates the presence of a symptom or a visual injury related to the relevant triage category and a "no" answer to one of the questions indicates the absence of a symptom or a visual injury related to the relevant triage category;
providing, with the computer, a plurality of tiers ranked according to urgency level, each of the plurality of tiers corresponding to one of a plurality of different triage dispositions, wherein a first "yes" answer received in response to any of the plurality of only yes/no questions directly results in selection with the computer of a disposition that corresponds to the tier which contains the affirmatively-answered question, the plurality of only yes/no questions and the plurality of dispositions designed to allow inquiry of the person by the triage operator when the person is located remotely from the triage operator;
sorting, by the computer, each of the only yes/no questions into the plurality of tiers based on a correlation that each of the questions has with the urgency level of each of the plurality of tiers; and
storing, by the computer, the plurality of only yes/no questions in relation to the corresponding plurality of dispositions in a database within the storage of the computer.

22. The method of claim 21, wherein the plurality of dispositions comprise:
emergent-911 transport by an emergency medical service to a medical provider;
emergent referral immediately to a medical provider;
urgent referral to a medical provider within about two days of the disposition being selected;
non-urgent referral to a medical provider within several days of the disposition being selected; and
self-care instructions.

23. The method of claim 22, further comprising:
providing interim self-care instructions to the person in anticipation of an eventual visit to a medical provider; and only reporting a call when no medical care is determined to be necessary.

24. The method of claim 21, wherein the questions are developed in accordance with a rule set.

25. The method of claim 24, wherein the rule set improves triage consistency.

26. The method of claim 21, wherein the questions are to be answered in the computer by the triage operator.

27. The method of claim 21, further comprising determining clinical frame questions that relate to a time, a place and a mechanism of injury.

28. The method of claim 21, further comprising:
providing triage to the person remotely, away from a treatment center or without access to medical equipment or a person with medical training, through a form of remote communication.

29. The method of claim 21, further comprising:
providing a plurality of additional questions to quantify responses to at least some of the plurality of yes/no questions so as to properly interpret the response as a "yes" or a "no."

30. A computer-implemented, triage category method for determining a medical triage disposition, the method executed by a computer including a processor and coupled with storage, the method comprising:
providing, by the computer to a triage operator, a set of tiered triage questions consisting of only yes/no questions arranged in a plurality of tiers, wherein the computer ranks the plurality of tiers according to a level of urgency;
providing, by the computer to the triage operator, a plurality of dispositions corresponding to the plurality of tiers, wherein a first "yes" answer received in response to any of the plurality of only yes/no questions directly results in selection by the computer of a disposition that corresponds to the tier which contains the affirmatively-answered question, and
wherein one of the plurality of dispositions is selected in response to a "no" response to a final triage question where all the prior responses were also "no," wherein the plurality of dispositions are final determinations whether and to what level of medical care a person undergoing triage is directed,
the plurality of only yes/no questions and the plurality of dispositions designed to allow inquiry of the person by the triage operator when the person is located remotely from the triage operator; and
storing the plurality of only yes/no questions in relation to the corresponding plurality of dispositions in a database within the storage of the computer.

31. The method of claim 30, wherein one of the plurality of dispositions is always selected after the questions are asked.

32. The method of claim 30, wherein one of the triage category and the set of tiered triage questions is developed in accordance with a rule set.

33. The method of claim 30, further comprising:
providing triage to the person remotely, away from a treatment center or without access to medical equipment or a person with medical training, through a form of remote communication.

34. The method of claim 30, wherein the selected disposition comprises self-care.

* * * * *

UNITED STATES PATENT AND TRADEMARK OFFICE
CERTIFICATE OF CORRECTION

| | |
|---|---|
| PATENT NO. | : 7,720,692 B2 |
| APPLICATION NO. | : 10/985850 |
| DATED | : May 18, 2010 |
| INVENTOR(S) | : Thomas H. Glimp et al. |

It is certified that error appears in the above-identified patent and that said Letters Patent is hereby corrected as shown below:

On the Title Page

Left column, item (75), after "Troyt M. Victorson," replace "Mundelein, IL (US)" with --Oakwood Hills, IL (US); Diane M. Kinch, Cary, IL (US); Wendy K. Biggerstaff, McHenry, IL (US); Joyce H. Zoiss, Silver Lake, WI (US)--.

In the Claims

In column 30, claim 21, line 28, before "questions consisting of" insert --of--.

Signed and Sealed this

Thirteenth Day of November, 2012

David J. Kappos
*Director of the United States Patent and Trademark Office*